US012740815B2

(12) United States Patent
Papannagari et al.

(10) Patent No.: US 12,740,815 B2
(45) Date of Patent: Sep. 22, 2026

(54) VARIABLE FIXATION BONE PLATES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Ramprasad Papannagari, Collierville, TN (US); Nicholas S. Ritchey, Collierville, TN (US); Paul Tornetta, III, Chestnut Hill, MA (US); William M. Ricci, New York, NY (US); Reza Firoozabadi, Mercer Island, WA (US); Hassan Mir, Tampa, FL (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/692,044

(22) PCT Filed: Sep. 15, 2022

(86) PCT No.: PCT/US2022/043642
§ 371 (c)(1),
(2) Date: Mar. 14, 2024

(87) PCT Pub. No.: WO2023/043909
PCT Pub. Date: Mar. 23, 2023

(65) Prior Publication Data

US 2024/0382241 A1 Nov. 21, 2024

Related U.S. Application Data

(60) Provisional application No. 63/245,036, filed on Sep. 16, 2021.

(51) Int. Cl.
*A61B 17/80* (2006.01)

(52) U.S. Cl.
CPC ...... *A61B 17/8052* (2013.01); *A61B 17/8066* (2013.01); *A61B 17/8085* (2013.01)

(58) Field of Classification Search
CPC ............ A61B 17/8066; A61B 17/8052; A61B 17/8085
See application file for complete search history.

(56) References Cited

U.S. PATENT DOCUMENTS 7,842,037 B2 11/2010 Schulze
8,603,091 B2 12/2013 Lutz
(Continued)

FOREIGN PATENT DOCUMENTS

CN 112107356 A 12/2020
EP 1295567 A1 3/2003
(Continued)

OTHER PUBLICATIONS

International Search Report and Written Opinion for International Application No. PCT/US2022/043642, filed Sep. 15, 2022, 12 pages.

(Continued)

*Primary Examiner* — Olivia C Chang
(74) *Attorney, Agent, or Firm* — KDW Firm PLLC

(57) ABSTRACT

A pelvic bone plate (100) includes a brim segment (101) coupled to a quadrilateral surface (QLS) segment (102) via at least one bridge (103). The brim segment is configured to be affixed directly adjacent to the pelvic brim. The QLS is configured to be arranged directly adjacent to the QLS of the pelvis. A plurality of slots (110-112) is arranged on the brim segment and the QLS segment. Each of the plurality of slots is configured to receive a fastener to affix the bone plate to the pelvis. The plurality of slots includes at least one of a non (Continued)

locking slot, a locking slot, and an elongated slot (112). The at least one elongated slot is configured to facilitate adjustment of the bone plate in an adjustment direction during an implantation procedure.

13 Claims, 19 Drawing Sheets

(56) References Cited

U.S. PATENT DOCUMENTS

| | | | | |
|---|---|---|---|---|
| 8,795,343 | B2 | 8/2014 | Stucki | |
| 9,358,053 | B2 | 6/2016 | Guy | |
| 9,713,485 | B2 | 7/2017 | Guy | |
| 2005/0165401 | A1 | 7/2005 | Pack | |
| 2012/0226279 | A1 | 9/2012 | Lutz | |
| 2013/0304124 | A1 | 11/2013 | Dube | |
| 2014/0257407 | A1 | 9/2014 | Cai | |
| 2014/0309690 | A1 | 10/2014 | Stucki | |
| 2016/0310180 | A1 | 10/2016 | Prybis | |
| 2017/0181784 | A1* | 6/2017 | Li | A61B 17/1728 |
| 2017/0319249 | A1* | 11/2017 | Guo | A61B 17/80 |
| 2021/0315616 | A1 | 10/2021 | Barrall | |
| 2022/0175427 | A1 | 6/2022 | Barrall | |
| 2024/0238019 | A1 | 7/2024 | Alabdulrahman | |

FOREIGN PATENT DOCUMENTS

| | | | |
|---|---|---|---|
| EP | 1737356 | B1 | 10/2012 |
| EP | 2772217 | A1 | 9/2014 |
| WO | 2023043909 | A1 | 3/2023 |

OTHER PUBLICATIONS

Synthes, "3.5 mm Low Profile Pelvic System—The comprehensive solution for pelvic fracture fixation," 2008, 19 pages.

Synthes, "In-situ Bending Instrument Set—For the adjustment of precontoured reconstruction plates during surgery," 2011, 4 pages.

DePuy Synthes, "Part of the 3.5 mm Low Profile Pelvic System—3.5 mm Quadrilateral Surface Plates," Surgical Technique, part of the Johnson & Johnson family of companies, Feb. 2017, 22 pages.

Stryker, "Matta Pelvic System—Pelvic and Acetabular Plating Plating," 2008, 3 pages.

R. J. Egli et al., "Secure Screw Placement in Management of Acetabular Fractures Using the Suprapectineal Quadrilateral Buttress Plate," Clinical Study, Hindawi, vol. 2017, Jun. 15, 2017, 13 pages. [online source] URL: https://www.hindawi.com/journals/bmri/2017/8231301/.

Stryker, "PRO—Pelvis and Acetabulum System," Operative technique, Content ID: PRO-ST-1 Rev 3, Jun. 2017, 48 pages.

www.medin.cz, "Omega pelvic plates," Medin, 2021, 5 pages. [online source] URL: https://www.medin.cz/en/omega.

International Search Report and Written Opinion for International Application No. PCT/US2025/042935, mailed on Nov. 14, 2025, 17 pages.

International Search Report and Written Opinion for International Application No. PCT/US2025/042922, mailed on Dec. 11, 2025, 17 pages.

* cited by examiner

VARIABLE FIXATION BONE PLATES

CROSS-REFERENCE TO RELATED APPLICATION

This application is a National Phase filing of International Application No. PCT/US2022/043642, filed Sep. 15, 2022, which application claims the benefit of U.S. Provisional Patent Application Ser. No. 63/245,036, filed Sep. 16, 2021, and titled "Variable Fixation Bone Plates," the entire contents of each application is hereby incorporated by reference in its entirety.

TECHNICAL FIELD

The present disclosure is directed to orthopedic implants, for instance, configured to be variably coupled to one or more patient bones, bone portions, bone fragments, and/or the like, and more specifically to bone plates for facilitating stabilization of fractures of the pelvis.

BACKGROUND

Bone fractures are often repaired by securing an orthopedic implant or device to one or more patient bone(s), bone portions, bone fragments, and/or the like (used interchangeably without the intent to limit). For example, treatment of acetabular fractures of the pelvis may include use of a bone plate to stabilize the bone to promote healing. However, minimal bone stock, limited anatomic access, and difficulty in obtaining stable internal fixation in the pelvis, particularly the quadrilateral surface, contribute to the surgical challenge of internal fixation using conventional bone plate devices. For example, the anatomical location of the quadrilateral plate is deep, and the bone is thin, surrounded by vital blood vessels and nerves, and is close to organs.

Accordingly, coupling a bone plate to a patient's bone such as, for example, a pelvic brim and/or quadrilateral surface of a pelvis, introduces a number of challenges that need to be overcome. For example, designing, contouring, and/or bending a bone plate that approximates the contour of the pelvic anatomy can be challenging. Bone plates that are too thick can be difficult to bend. However, bone plates that are sufficiently flexible to facilitate easier bending, either pre-operative or inter-operative, may not provide adequate strength. Moreover, bending bone plates requires significant skill and is challenging to achieve a proper fit.

To alleviate some of these concerns, some manufacturers provide large sets or kits of bone plates to provide surgeons with different bone plate sizes and shapes. However, this has its own disadvantages due to the large number of plates needed per set, which increases costs and complexity. In addition, conventional bone plates do not include a screw hole or slot pattern that allows for efficient and accurate adjustment of the implanted bone plate during an implantation procedure.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an improved bone plate arranged and configured for use in bone fractures, including, without limitation, acetabular fractures or quadrilateral plate fractures of the pelvis. For example, in some examples, the bone plate may be in the form of a pelvic bone plate, including, for instance, a suprapectineal bone plate or an infrapectineal bone plate. In either event, the bone plate is designed and configured for inter-operative dynamic adjustment to facilitate an optimal fit of the bone plate adjacent to the pelvis.

In use, the bone plate is arranged and configured to fit or be easily bent to fit, either pre-operatively or inter-operatively, to stabilize the patient's bone such as, for example, a patient's pelvis.

In any preceding or subsequent example, the bone plate may include a brim segment coupled to a quadrilateral surface (QLS) segment. The brim segment may be arranged, contoured, and/or otherwise configured to be arranged directly adjacent to the pelvic brim. The QLS segment may be arranged, contoured, and/or otherwise configured to be arranged directly adjacent to the QLS of the pelvis.

In any preceding or subsequent example, the brim segment may be arranged and configured to approximate the contours of at least a portion of the pelvic brim when implanted. In any preceding or subsequent example, the QLS segment may be arranged and configured to approximate the contours of at least a portion of the QLS of the pelvis when implanted. In any preceding or subsequent example, the QLS segment may have a substantially triangular shape formed of a plurality of sub-segments.

In any preceding or subsequent example, a plurality of slots may be arranged on the brim segment and the QLS segment. Each of the plurality of slots may be configured to receive a fastener to affix the bone plate to the pelvis. In any preceding or subsequent example, the plurality of slots may include at least one of a non-locking slot, a locking slot, a variable-angle slot, and an elongated slot. In any preceding or subsequent example, the plurality of slots may include at least one non-locking slot and at least one locking slot. In any preceding or subsequent example, the plurality of slots may include at least one non-locking slot, at least one locking slot, and at least one elongated slot.

In any preceding or subsequent example, the plurality of slots may include at least one elongated slot. The at least one elongated slot may be configured to facilitate adjustment of the bone plate in an adjustment direction during an implantation procedure. In any preceding or subsequent example, the adjustment direction may be one of a medial/lateral direction or a superior/inferior direction. The elongated slots may allow a surgeon to hold the bone plate in place via fasteners inserted through the elongated slots, while also allowing for adjustments, for example, via shifting of the bone plate.

In any preceding or subsequent example, the bone plate may include one elongated slot arranged on the brim segment. In any preceding or subsequent example, the bone plate may include one elongated slot arranged on the QLS segment. In any preceding or subsequent example, the bone plate may include at least one elongated slot on the brim segment and at least one elongated slot on the QLS segment.

In any preceding or subsequent example, the bone plate may include at least one elongated slot on the brim segment and at least one elongated slot on the QLS segment, and the at least one elongated slot on the brim segment has a different adjustment direction than the at least one elongated slot on the QLS segment.

In any preceding or subsequent example, the bone plate may include at least one elongated slot on the brim segment and at least one elongated slot on the QLS segment, and the at least one elongated slot on the brim segment has the adjustment direction of medial/lateral and the at least one elongated slot on the QLS segment has the adjustment direction of superior/inferior.

In any preceding or subsequent example, the plurality of slots may be arranged in a slot pattern. In any preceding or subsequent example, the slot pattern may include a brim pattern of slots on the brim segment and/or a QLS pattern of slots on the QLS segment.

In any preceding or subsequent example, the brim pattern may include a plurality of locking slots, a plurality of non-locking slots, and at least one elongated slot. In any preceding or subsequent example, the brim pattern may include an alternating slot pattern of alternating locking slots and non-locking slots along a longitudinal length of the brim segment. In any preceding or subsequent example, at least one elongated slot may be arranged between a locking slot and a non-locking slot of the alternating slot pattern.

In any preceding or subsequent example, the QLS slot pattern may include a plurality of locking slots. In any preceding or subsequent example, the QLS slot pattern may include a plurality of locking slots without a non-locking slot. In any preceding or subsequent example, the QLS slot pattern may include at least one elongated slot. In any preceding or subsequent example, the QLS slot pattern may include at least one slot arranged on each sub-segment.

In any preceding or subsequent example, the plurality of slots may be arranged in a plurality of sets. Each set may include a plurality of elongated slots configured to provide a certain direction of movement. In any preceding or subsequent example, a medial/lateral set may be used to facilitate medial/lateral movement of the bone plate about the pelvis. In any preceding or subsequent example, a superior/inferior set may be used to facilitate superior/inferior movement of the bone plate about the pelvis. In some examples, a set may be configured to provide for a different freedom of movement, such as a movement length (e.g., a first set may allow 2 mm of movement, a second set may allow 5 mm of movement, and so on).

In any preceding or subsequent example, the slot pattern may include a brim elongated slot arranged on the brim segment at a slot orientation angle X with respect to a QLS elongated slot arranged on the QLS segment. In any preceding or subsequent example, slot orientation angle X may be about 0 degrees (e.g., the longitudinal axes of the brim elongated slot and the QLS elongated slot are parallel or substantially parallel). In any preceding or subsequent example, slot orientation angle X may be about 90 degrees (e.g., the longitudinal axes of the brim elongated slot and the QLS elongated slot are perpendicular or substantially perpendicular). In any preceding or subsequent example, slot orientation angle X may be about 5 degrees, about 10 degrees, about 15 degrees, about 30 degrees, about 45 degrees, about 90 degrees, or about 150 degrees.

In any preceding or subsequent example, the elongate slots may have a slot length (e.g., extending longitudinally from a first end of the elongated slot to the opposite end of the elongated slot) of about 3 mm, about 5 mm, about 7 mm, about 10 mm, about 20 mm, and any value or range between any of the foregoing (including endpoints).

In any preceding or subsequent example, at least a portion of the plurality of slots arranged on the brim segment may be configured to receive different sized fasteners compared with at least a portion of the plurality of slots arranged on the QLS segment. In any preceding or subsequent example, the size of the fasteners may be about 2.0 mm, about 2.5 mm, about 2.7 mm, about 3.0 mm, about 3.5 mm, about 4.0 mm, about 4.5 mm, about 4.7 mm, about 5.0 mm, about 5.5 mm, about 6.0 mm, about 6.5 mm, about 6.7 mm, about 7.0 mm, about 8.0 mm, about 9.0 mm, about 10.0 mm, and any value or range between any of the foregoing (including endpoints). In any preceding or subsequent example, at least a portion of the plurality of slots arranged on the brim segment may be configured to accommodate 3.5 mm fasteners and at least a portion of the plurality of slots arranged on the QLS segment may be configured to accommodate 2.7 mm fasteners.

In any preceding or subsequent example, the bone plate may include a hole pattern arranged and configured to utilize variable angled slots to facilitate positioning of the bone plate over a portion of bone. In addition, the variable angled slots may be configured for polyaxial receiving of one or more bone fasteners.

In any preceding or subsequent example, the slot pattern may be based on an implantation procedure used to implant the bone plate. In any preceding or subsequent example, the configuration of the slot pattern may be configured to allow access to the elongated slots via incisions made during the implantation procedure.

In any preceding or subsequent example, a bone plate may include a brim segment coupled to a QLS segment via at least one bridge. The brim segment may be configured to be affixed directly adjacent to the pelvic brim. The QLS segment may be configured to be arranged directly adjacent to the QLS of the pelvis. A plurality of slots may be arranged on the brim segment and the QLS segment. Each of the plurality of slots may be configured to receive a fastener to affix the bone plate to the pelvis. The plurality of slots may include at least one of a non-locking slot, a locking slot, and an elongated slot. The at least one elongated slot may be configured to facilitate adjustment of the bone plate in an adjustment direction during an implantation procedure. The adjustment direction may be one of a medial/lateral direction or a superior/inferior direction.

In any preceding or subsequent example, a bone plate implantation process or method may be performed for implanting a bone plate configured according to some examples herein. In any preceding or subsequent example, the bone plate implantation method may be performed by an operator (for example, a surgeon), a logic device (for example, a computer assisted surgery system (CASS)), or a combination thereof. In any preceding or subsequent example, the method may include determining a bone plate configuration (e.g., shape, size, contour, and/or the like), determining a slot pattern for the bone plate, implanting the bone plate, loosely affixing the bone plate to the bone via at least the elongated slots, adjusting the bone plate by shifting the bone plate about the elongated slots to achieve an optimal fit, and rigid fixation of the bone plate to the bone with the optimal fit.

In some examples, a pelvic bone plate may include a brim segment coupled to a quadrilateral surface (QLS) segment via at least one bridge, wherein the brim segment is configured to be affixed to a portion of a pelvis of a patient and the QLS segment is configured to be arranged directly adjacent to a QLS of the pelvis, and a plurality of slots arranged on the brim segment, at least a portion of the plurality of slots configured to receive a fastener to affix the bone plate to the pelvis, the plurality of slots comprising at least one elongated slot configured to receive the fastener to non-rigidly affix the pelvic bone plate to the pelvis to facilitate adjustment of the bone plate in an adjustment direction during an implantation procedure.

In any preceding or subsequent example, the adjustment direction may be one of a medial/lateral direction or a superior/inferior direction.

In any preceding or subsequent example, the at least one elongated slot may include a short dimension configured to prevent movement of the pelvic bone plate in a short direction when a fastener is arranged within the at least one elongated slot, and a long dimension configured to allow movement of the pelvic bone plate in the adjustment direction when the pelvic bone plate is non-rigidly affixed to the pelvis.

In any preceding or subsequent example, the pelvic bone plate is a suprapectineal bone plate wherein the brim segment is configured to be affixed on the pelvic brim.

In any preceding or subsequent example, the pelvic bone plate is an infrapectineal bone plate wherein the brim segment is configured to be affixed to the QLS below the pelvic brim.

In any preceding or subsequent example, at least a portion of the plurality of slots may be arranged on the QLS segment.

In any preceding or subsequent example, the plurality of slots may include at least one elongated slot arranged on the QLS segment.

In any preceding or subsequent example, the plurality of slots may include at least one non-locking slot and at least one locking slot.

In any preceding or subsequent example, the plurality of slots may be arranged on the brim segment in a brim slot pattern comprising alternating locking slots and non-locking slots arranged along a longitudinal length of the brim segment.

In any preceding or subsequent example, the brim slot pattern may include at least one elongated slot arranged between a locking slot and a non-locking slot of the brim slot pattern.

In any preceding or subsequent example, the plurality of slots may include at least one set of elongated slots configured to facilitate movement in one adjustment direction.

In any preceding or subsequent example, the at least one set may include one of a medial/lateral adjustment set or a superior/inferior adjustment set.

In any preceding or subsequent example, the at least one elongated slot may include a plurality of slots arranged at a slot orientation angle.

In any preceding or subsequent example, at least a portion of the plurality of slots may include a variable angled slot configured to receive a variable angled bone fastener.

In any preceding or subsequent example, the at least one elongated slot may be configured to facilitate movement of about 1 mm to about 10 mm.

Exemplary embodiments of the present disclosure provide numerous advantages. For example, by incorporating one or more features of the present disclosure, surgeons are provided with increased options for securing a bone plate across a pelvic fracture. In addition, and/or alternatively, by incorporating one or more features of the present disclosure, the bone plates are arranged and configured to facilitate easier insertion with reduced soft tissue irritation. In addition, and/or alternatively, by incorporating one or more features of the present disclosure, the bone plates are arranged and configured to facilitate better positioning of the bone plate against the patient's bone, for example, by supporting dynamic inter-operative adjustments of the bone plate. In addition, and/or alternatively, by incorporating the particular type and configuration of slots, including, without limitation, elongated slots, some example embodiments may provide a variable fixation bone plate configured to allow for dynamic adjustment of the fixation properties of a bone plate post-insertion into the patient.

Further features and advantages of at least some of the example embodiments of the present invention, as well as the structure and operation of various example embodiments of the present invention, are described in detail below with reference to the accompanying drawings.

BRIEF DESCRIPTION OF THE DRAWINGS

By way of example, specific examples of the disclosed device will now be described, with reference to the accompanying drawings, in which.

Figure 1A:
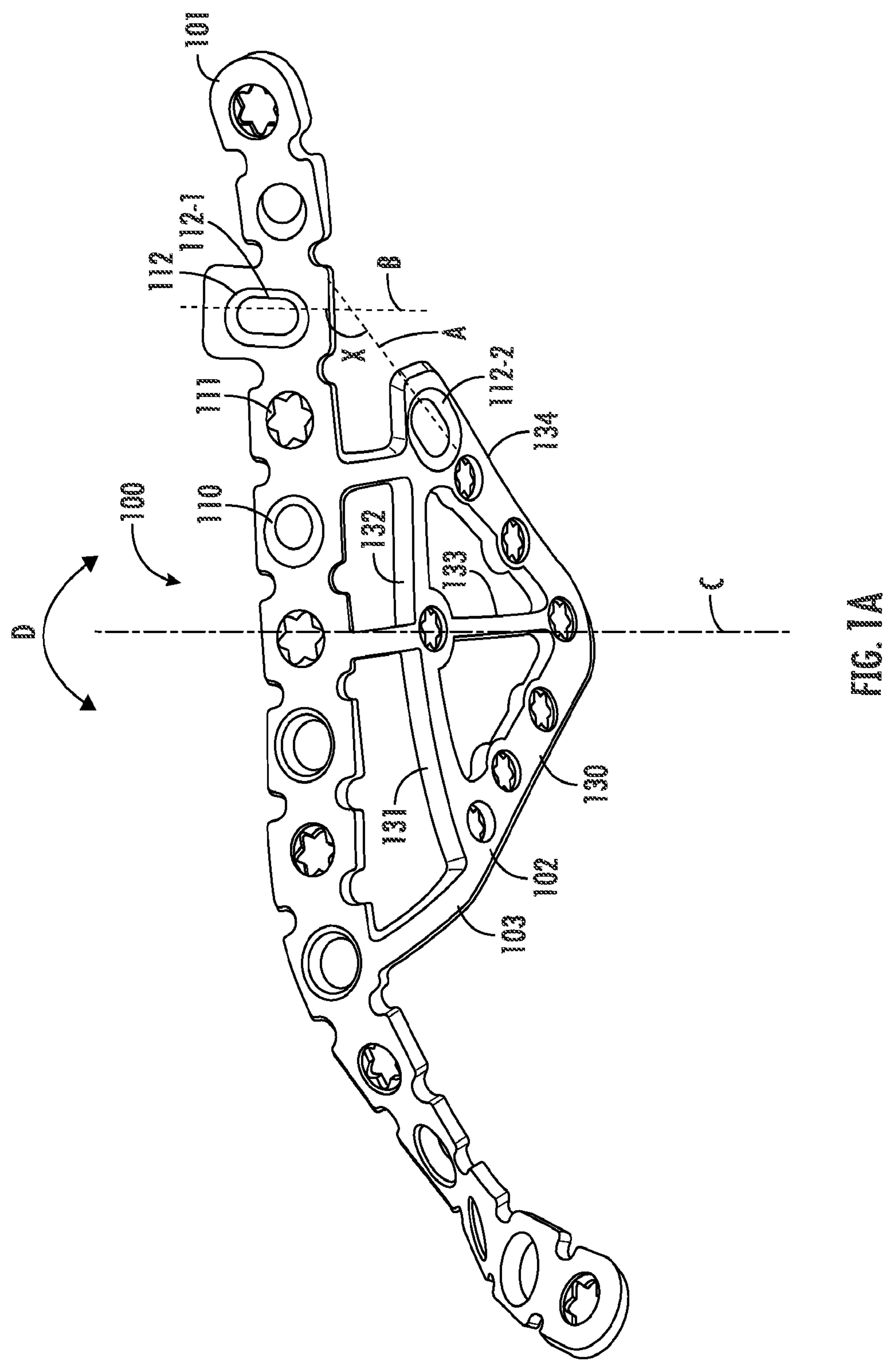
FIG. 1A depicts a perspective view of a suprapectineal bone plate in accordance with the present disclosure.

It should be understood that the drawings are not necessarily to scale and that the disclosed examples are sometimes illustrated diagrammatically and in partial views. In certain instances, details which are not necessary for an understanding of the disclosed methods and devices, or which render other details difficult to perceive may have been omitted. It should be further understood that this disclosure is not limited to the particular examples illustrated herein. In the drawings, like numbers refer to like elements throughout unless otherwise noted.

DETAILED DESCRIPTION

Various features or the like of orthopedic bone plates will now be described more fully hereinafter with reference to the accompanying drawings, in which one or more features of the bone plates will be shown and described. It should be appreciated that the various features or the like described hereinafter may be used independently of, or in combination, with each other. It will be appreciated that a bone plate as disclosed herein may be embodied in many different forms and should not be construed as being limited to the examples set forth herein. Rather, these examples are provided so that this disclosure will convey certain features of the bone plate to those skilled in the art.

Disclosed herein are bone plates including one or more features for enabling, inter alia, increased flexibility, conformity, and fixation for coupling the bone plates to bone, particularly the quadrilateral surface and/or pelvic brim (acetabular rim or brim, pelvic rim or brim, or iliopectineal line; used interchangeably without the intent to limit) of a human pelvis.

Pelvic fractures pose unique fixation challenges. For example, the anatomical location of the quadrilateral plate is deep, and the bone is thin, surrounded by vital blood vessels and nerves, and is close to organs. Conventional bone plates have been inadequate in buttressing pelvic fractures to provide the proper support to reset comminuted areas of the fractured bone. More specifically, it is challenging for a surgeon to effectively adjust the implant location to achieve an optimal fit within the quadrilateral surface and/or along the pelvic brim. As such, pelvic bone plates are typically implanted with suboptimal placement, which may often lead to poor patient outcomes.

As such, as will be described herein, the present disclosure discloses a bone plate including one or more features that may be used in combination or singularly, these features are designed and configured to provide increased flexibility in enabling a surgeon to position and/or secure a bone plate across a fracture of a patient pelvic bone. In addition, and/or alternatively, one or more features may be provided to facilitate easier insertion of the bone plate along the patient's bone and/or to provide improved contouring to facilitate better positioning of the bone plate against the patient's bone (e.g., better contouring with the quadrilateral surface and/or pelvic brim). In addition, and/or alternatively, by incorporating the particular type and configuration of slots, including, without limitation, elongated slots, some examples may provide a variable fixation bone plate configured to allow for dynamic adjustment of the implantation location and/or orientation of a bone plate post-insertion into the patient during a surgical procedure. For example, the bone plate may be non-rigidly affixed to the bone (i.e., screws are inserted through the elongated slots, but not fully tightened), to allow the bone plate to be held in place, while allowing a surgeon to make fine adjustments in-place during an implantation procedure.

In some examples, a bone plate may include one or more segments configured to be affixed to specific regions of a pelvis. For example, a bone plate may include a quadrilateral surface (QLS) segment configured to be affixed to the QLS of a pelvis. In another example, a bone plate may include a brim segment configured to be affixed on or adjacent to the pelvic brim (for instance, the acetabular brim). In various examples, a bone plate may include various slots, holes, sleeves, apertures, or other openings configured to receive various fasteners and/or surgical implantation tools for affixing the bone plate to patient bone. In some examples, the slots may be configured to receive fasteners and may include non-locking slots, locking slots, elongated slots, countersunk slots, and/or combinations thereof. In some examples, one or more slots may include variable-angle slots configured to receive a fastener at an angle. Non-limiting angles may include about 25 degrees, about 10 degrees, about 10 degrees, about 75 degrees, and any value or range between any of the foregoing (including endpoints).

In some examples, elongated slots may allow variable positioning of a screw within the slot. More specifically, elongated slots may allow for medial/lateral movement, superior/inferior movement, angular movement (or rotation), and other repositioning of the bone plate.

As will be described herein, a bone plate may have various shapes, sizes, and/or configurations of other physical properties. It should be appreciated that the bone plate may be provided in any suitable shape and/or configuration, which, as will be appreciated by one of ordinary skill in the art, may be dependent on the location and type of patient bone being fixed. For example, a bone plate may include various bone conforming segments configured to correspond with different anatomical features. In addition, the bone plate may be arranged and configured to span, contact, be affixed to, and/or the like various portions of a human pelvis, including without limitation, the QLS, pelvic brim, and/or other adjacent anatomical features.

As will be described herein, the bone plate may include any now known or hereafter developed additional features. The bone plate may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some examples, the bone fastener may be manufactured from the same material as the bone plate. In other examples, the bone fasteners may be manufactured from a different material as compared to the bone plate.

The fastener can be any type of fastener now known or hereafter developed. For example, the fastener may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the fastener can include any surface that will engage with and seat within a locking screw opening formed in the bone plates. For example, the head portion can include threads. Alternatively, the head portion can include a series of dimples, ridges, bumps, protrusions, textured areas, or any other surface that can secure the fastener.

The fastener may be any typical fastener, made out of any appropriate material. The fastener may include a bore for receiving a driver in order to drive the fastener through the bone plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the bone plate and into the patient's bone.

The shaft of the fastener may be fully threaded, partially threaded, or a helical blade, and/or may include one or more tacks, deployable talons, expandable elements, protrusions, or any feature that allows the shaft to engage the patient's bone. It is also possible that shaft be non-threaded so that the fastener takes the form of a peg or a pin. This alternative implementation may be preferred in certain procedures where, for instance, the main goal is to prevent tilting of a bone segment or in procedures where there is no concern of the fastener pulling out from the patient's bone and hence no need for the shaft to be threaded or otherwise configured to engage the patient's bone. The end of the shaft may be a self-tapping or self-drilling tip.

The fasteners may be of different dimensions, including length and/or outer diameter. For example, fasteners may have an outer diameter of about 1.0 millimeters (mm), about 2.0 mm, about 2.7 mm, about 3.0 mm, about 3.5 mm, about 4.0 mm, about 5.0 mm, and any value or range of the foregoing (including endpoints).

In any event, as will be readily apparent from the remaining disclosure, the focus of the present disclosure is on examples of bone plates including one or more features arranged and configured to provide increased flexibility for positioning and securing the bone plate on, within, adjacent to and/or the like various portions of a human pelvis, including, without limitation the QLS and/or pelvic brim.

In addition, the bone plate may include one or more features arranged and configured to enable implantation of the bone plate against a patient's pelvic bone using various implantation procedures while, among other advantages, minimizing irritation of the patient's soft tissue and one or more features to provide improved contouring to facilitate better positioning of the bone plate against the patient's bone. Non-limiting examples of implantation procedures may include a middle window approach, a Stoppa approach, a modified Stoppa approach, an anterior approach, an ilio-inguinal (IL) approach, and/or the like.

Although pelvic bone plates are used in some examples in the present disclosure, examples are not so limited. Therefore, it should be appreciated that the present disclosure should not be limited to any particular configuration of bone plate and/or insertion procedure unless specifically claimed. In addition, while the present disclosure will be described and shown as being directed to a pelvic fixation plate, it should be appreciated that features of the present disclosure have applicability and may be used in connection with other bone plates such as, for example, humerus plates, femur plates, tibia plates, etc. For example, a femoral plate may include elongated slots to allow for fine, in-place adjustment of the plate during an implantation procedure. As such, the present disclosure should not be limited to any specific bone plate or bone plate configuration unless expressly claimed.

FIG. 1A depicts a perspective view of a suprapectineal bone plate in accordance with the present disclosure. As shown in FIG. 1A, a bone plate 100 may include a brim segment 101 coupled to a QLS segment 102 via one or more bridges, posts, connecting segments, and/or the like 103. Although bone plate 100 includes a plurality of bridges 103, only one is labelled to simplify the figure. In some examples, bridges 103 may be malleable to allow for changing the relative positions of the brim segment 101 and the QLS segment 102 to achieve an optimal fit.

As will be described herein, bone plate 100 may be in the form of a pelvic bone plate. That is, bone plate 100 may be arranged and configured for positioning adjacent to the pelvis of a patient, in particular, within the interior surface of the pelvis adjacent to the QLS and pelvic brim (see, for example, FIG. 1B). In addition, as will be described herein, bone plate 100 may include one or more features so that bone plate 100 facilitates dynamic positioning and securement to a patient's pelvis during a surgical procedure.

In addition, as will be described herein, bone plate 100 may include one or more features so that the bone plate 100 facilitates easier insertion such as, for example, percutaneous insertion, with reduced soft tissue irritation. In addition, and/or alternatively, bone plate 100 may include one or more features to provide improved contouring to facilitate better positioning of the bone plate against the patient's bone.

Figure 1B:
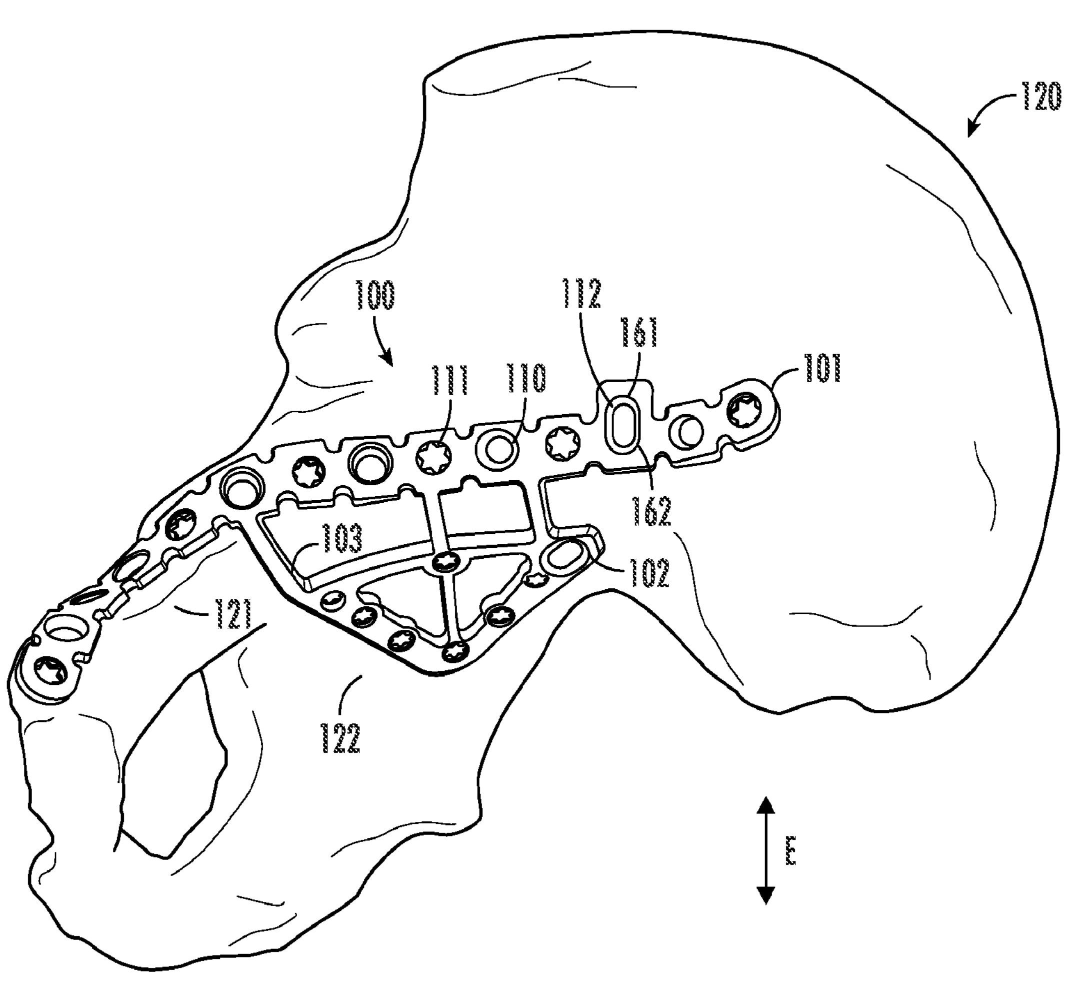
FIG. 1B depicts the suprapectineal bone plate of FIG. 1A implanted on a pelvis in accordance with the present disclosure.
Figure 2A:
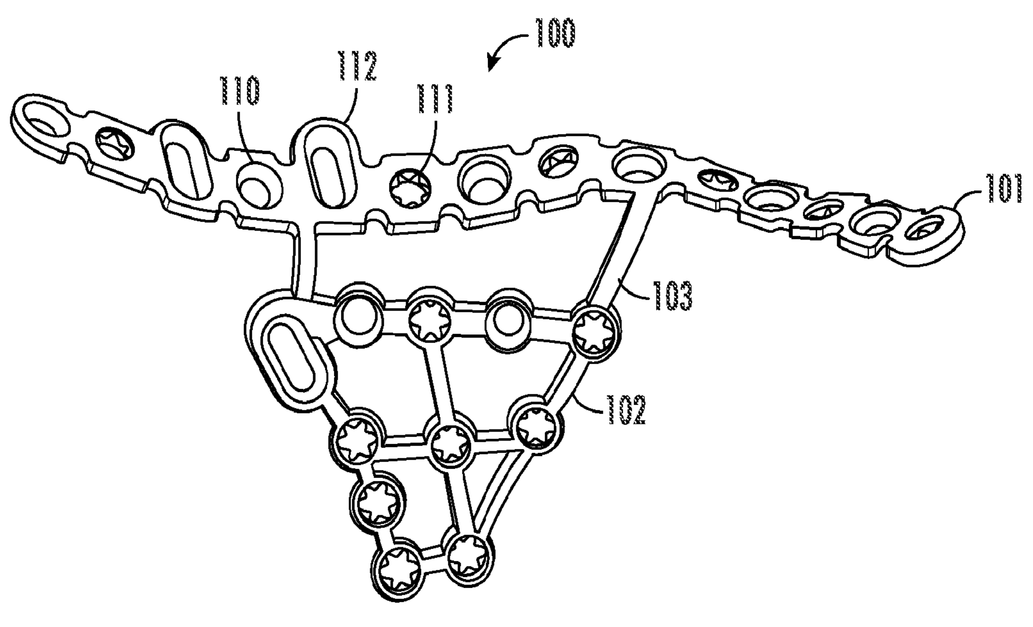
FIGS. 2A-2F depict multiple views of a suprapectineal bone plate in accordance with the present disclosure.
Figure 2B:
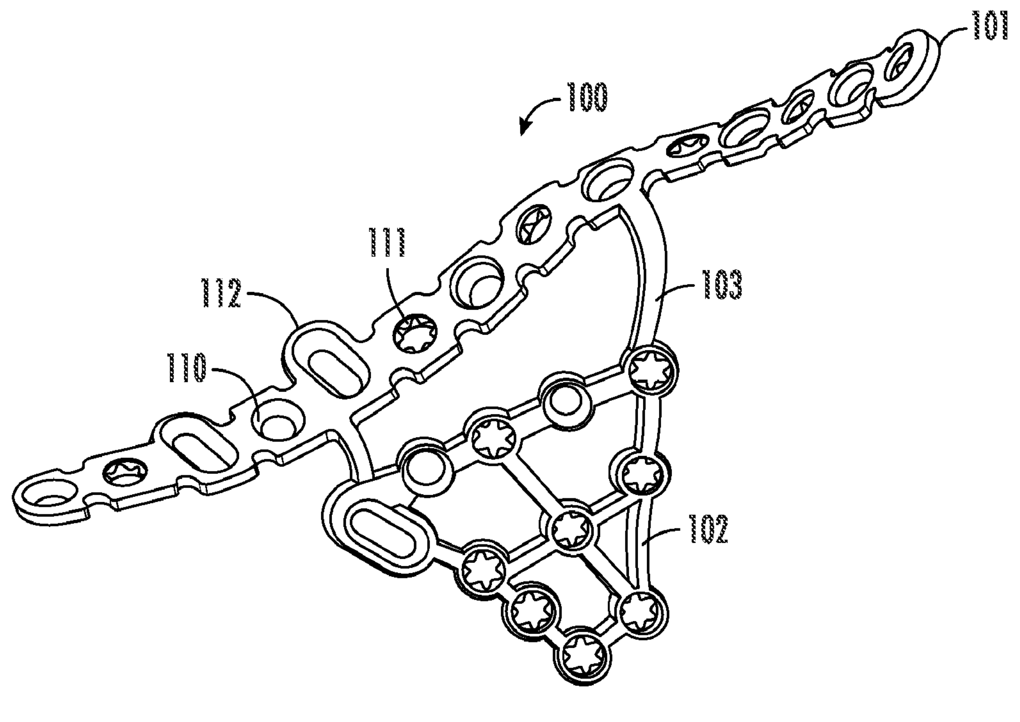
Figure 2C:
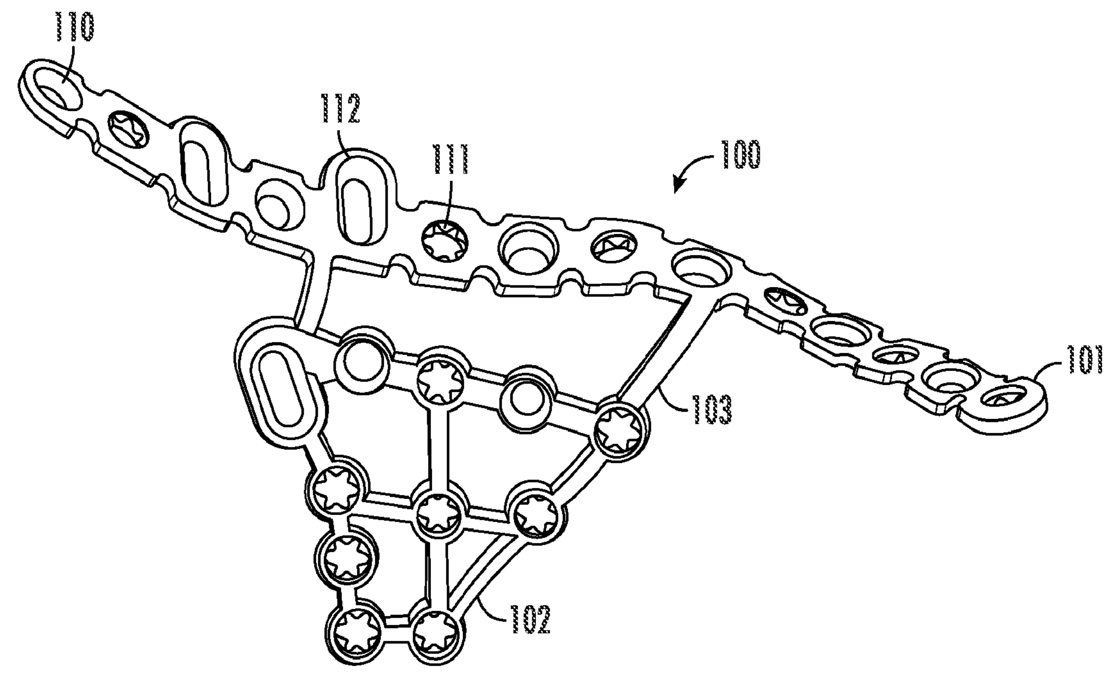
Figure 2D:
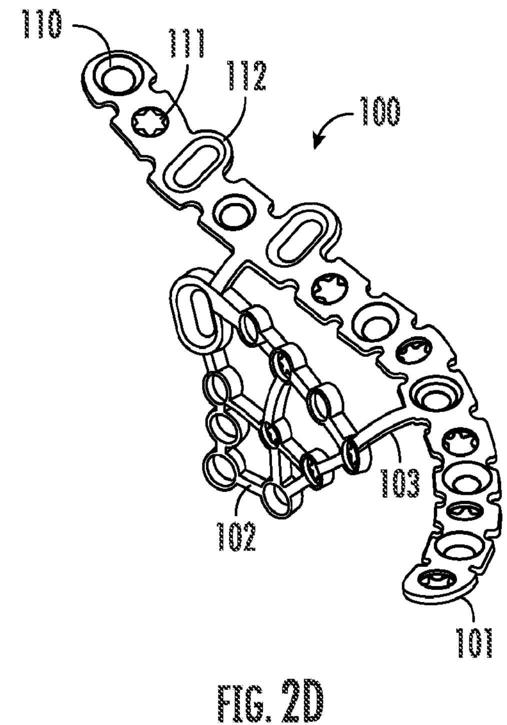
Figures 2E, 2F:
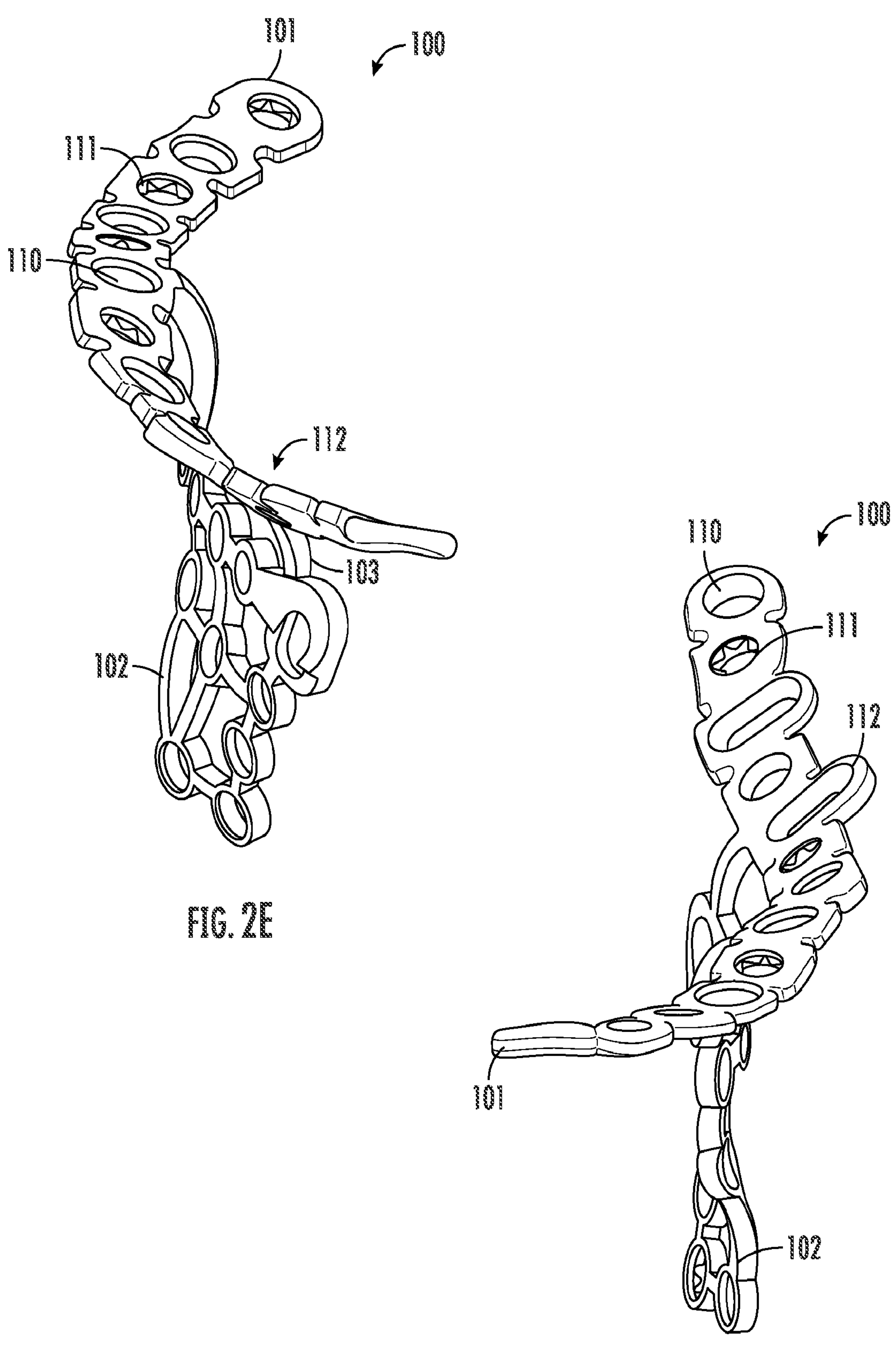

In some examples, bone plate 100 may be formed as a suprapectineal plate in which brim segment 101 is configured to be arranged on or over the pelvic brim. Referring to FIG. 1B, therein is depicted bone plate 100 of FIG. 1A implanted on a pelvis 120 in accordance with the present disclosure. As shown in FIG. 1B, brim segment 101 may be arranged to contour, conform, or otherwise correspond over pelvic brim 121 of pelvis 120 (in contrast, see FIGS. 4A-4F and 5 for an infrapectineal plate). QLS segment 102 may be configured to be affixed on or directly adjacent to a QLS 122 of pelvis 120.

In some examples, bone plate 100 may include one or more slots 110-112 of various types. Non-limiting examples of slots may include non-locking slots 110, locking slots 111, elongated slots 112, and/or variable-angle forms thereof. Although a plurality of each type of slot 110-112 is depicted in FIGS. 1A and 1B, only one is labeled to simplify the figure.

In some examples, brim segment 101 may be or may include a portion having a series of slots 110-112 arranged in a surface thereof. Brim segment 101 may be configured to follow or substantially follow the contour of, and run longitudinally along, at least a portion of pelvic brim 121. Brim segment 101 may be contoured to conform or substantially conform to a shape along a fixation location on pelvic brim 121. Brim segment 101 may have various widths and lengths according to some examples. Non-limiting examples of widths may include about 3 mm, about 4 mm, about 5 mm, about 10 mm, and any value or range between any of the foregoing (including endpoints). Illustrative and non-restrictive examples of lengths may include about 10 mm, about 20 mm, about 30 mm, about 40 mm, about 50 mm, about 100 mm, about 110 mm, about 120 mm, about 130 mm, about 140 mm, about 150 mm, and any value or range between any of the foregoing (including endpoints). In some examples, for example, the length of brim segment 101 may be of sufficient length to extend from the iliac fossa to the pubic ramus of the pelvis.

In addition, a distance between slots ("slot distance") may be configured according to some examples. For example, a slot distance may be about 1 mm, about 2 mm, about 3 mm, about 4 mm, about 5 mm, about 10 mm, about 15 mm, about 20 mm, about 25 mm, about 30 mm, and any value or range between any of the foregoing (including endpoints). In some examples, the slot distance may be different on brim segment 101 compared with QLS segment 102.

Elongated slots 112 may have a slot length (e.g., referring to FIG. 1B, extending longitudinally from a first end 161 of the elongated slot to the opposite end 162 of elongated slot 112) configured according to some examples. In various examples, the slot length may be about 3 mm, about 5 mm, about 7 mm, about 10 mm, about 15 mm, about 20 mm, about 25 mm, and any value or range between any of the foregoing (including endpoints).

In general, elongated slots 112 are longer in one dimension (for instance, length compared with width). For instance, elongated slots 112 may have a short dimension that contacts an inserted fastener on both sides (or with minimal movement) to prevent or substantially prevent movement of bone plate 100 in the short dimension, and a long dimension (e.g., from end 161 to end 162; perpendicular to the short dimension) where both sides do not contact the inserted fastener without substantive movement of bone plate 12 to facilitate movement in the long dimension. When a fastener is inserted through an elongated slot 112, movement in the short direction may be prevented or substantially prevented (i.e., the sides of the short dimension contact the fastener). However, movement in the long direction is allowed to facilitate shifting of the bone plate 100 when a fastener is inserted through an elongated slot 112 and into the bone of pelvis 120. In some examples, elongated slots 112 may have an oval or substantially oval shape (compared with a circular slot).

In some examples, QLS segment 102 may be shaped to conform or partially conform to a portion of QLS 122. In various examples, QLS segment 102 may include or may have a triangular or substantially triangular shape (i.e., a closed, two-dimensional shape with three sides, three angles, and three vertices), although other shapes or forms are contemplated in the present disclosure. In some examples, QLS segment 102 may be formed of a plurality of segments (or sub-segments), such as segments 130-134. In various examples, one or more of segments 130-134 may include slots 110-112. In some examples, QLS segment 102 may not include any slots 110-112 (for instance, QLS segment 102 may include segments 130-134 without slots 110-112).

In some examples, slots 110-112 may be sized to accommodate different size fasteners. Non-limiting examples may include slots 110-112 configured to receive about 2.7 mm fasteners or about 3.5 mm fasteners. In various examples, different sized slots 110-112 may be arranged on brim segment 101 compared with QLS segment 102. For example, slots 110-112 on brim segment 101 may accommodate 3.5 mm fasteners and slots 110-112 on QLS segment 102 may accommodate 2.7 mm fasteners.

In various examples, at least one of brim segment 101 and QLS segment may include an elongated slot 112. Elongated slot 112 may be sized to allow a certain degree of movement or length of movement about a fastener extending therethrough and into the pelvic bone (but not fully tightened to allow movement). For example, the length of substantive movement (for example, without the intent to limit, referring to FIG. 1B, in direction E (or substantially in direction E)), may be about 0.5 mm, about 1 mm, about 2 mm, about 3 mm, about 4 mm, about 5 mm, about 10 mm, and any value or range between any of the foregoing (including endpoints). In another example, the degree of substantive movement (for instance, a degree of rotation through a longitudinal axis extending through a middle of bone plate 100) may be about 1 degree, about 2 degrees, about 3 degrees, about 4 degrees, about 5 degrees, about 10 degrees, and any value or range between any of the foregoing (including endpoints).

In some examples, brim segment 101 may include one elongated slot 112. In various examples, brim segment 101 may include a plurality of elongated slots 112. In some examples, QLS segment 102 may include one elongated slot 112. In various examples, QLS segment 102 may include a plurality of elongated slots 112. In some examples, brim segment 101 and/or QLS segment may include 1 elongated slot 112, 2 elongated slots 112, 3 elongated slots 112, 4 elongated slots 112, 5 elongated slots 112, 10 elongated slots 112, or any value or range between any two of these values (including endpoints). Examples are not limited in this context.

In some examples, elongated slots 112 may have a bone plate orientation, for example, with respect to bone plate 100. For example, slots 112-1 (a brim elongated slot) and 112-2 (a QLS elongated slot) may be arranged in different planes with respect to each other. In one example, referring to FIG. 1A, the bone plate orientation may be with respect to a line C running vertically through the middle of bone plate 100. However, the bone plate orientation of elongated slots 112 may be determined relative to other dimensions, for example, a line running longitudinally through bone plate 100 (not shown), a segment, and/or the like. For example, line B runs longitudinally or lengthwise through slot 112-1. In some examples, line B may be parallel or substantially parallel with line C. In another example, line B may be orientated 10 degrees from line C (for instance, an angle created by the intersection of line B and line C). Line B may be orientated at various angles with respect to line C, including, without limitation, 0 degrees (parallel or substantially parallel), 1 degree, 5 degrees, 10 degrees, 20 degrees, 30 degrees, 40 degrees, 45 degrees, 50 degrees, 60 degrees, 90 degrees (perpendicular or substantially perpendicular), 120 degrees, 150 degrees, and any value or range between any of the aforementioned values (including endpoints).

In addition, elongated slots 112 may have an inter-slot orientation with respect to each other. For example, referring to FIG. 1A, elongated slot 112-1 and elongated slot 112-2 may have lines A and B running longitudinally or lengthwise therethrough, respectively. Intersection of lines A and B may form slot orientation angle X, providing an inter-slot orientation between elongated slot 112-1 and elongated slot 112-2. In some examples, brim segment 101 may have at least one elongated slot (such as slot 112-1) and QLS segment 102 may have at least one elongated slot (such as slot 112-2). Slot 112-1 and slot 112-2 may have an inter-slot orientation that is parallel or substantially parallel, perpendicular or substantially perpendicular, and/or angles between parallel and perpendicular. Non-limiting examples of inter-slot orientation angles may include about 0 degrees (i.e., parallel or substantially parallel), about 1 degree, about 5 degrees, about 10 degrees, about 20 degrees, about 30 degrees, about 40 degrees, about 45 degrees, about 50 degrees, about 60 degrees, about 90 degrees (i.e., perpendicular or substantially perpendicular), about 120 degrees, about 150 degrees, and any value or range between any of the aforementioned values (including endpoints).

In some examples, QLS segment 102 may have an elongated slot 112 on one segment 130-134, such as segment 134. In other examples, QLS segment 102 may have one or more elongated slots on one or more of segments 130-134.

Slots may be in the form of a locking slot or locking screw slot 111. That is, as will be appreciated by one of ordinary skill in the art, locking slots 111 may include a plurality of threads formed on an inner surface thereof for mating with threads formed on an outer surface of a head portion of a bone fastener. Thus arranged, the bone fastener may be said to be locked to bone plate 100 via locking slots 111. That is, as will be appreciated by one of ordinary skill in the art, the bone fastener is threaded through one of locking slots 111 formed in bone plate 100 and into the patient's bone. The bone fastener is secured to bone plate 100 via threads formed on the head portion of the bone fastener that cooperate with threaded locking slot 111 formed in bone plate 100. This secures bone plate 100 with respect to the patient's bone and provides rigid fixation between bone plate 100 and the bone fasteners. That is, because the head portion of the bone fastener interdigitates with the threads formed in locking slots 111 of bone plate 100, bone plate 100 and the fasteners form a stable system or construct, and the stability of the fracture can be dependent on or aided by the stiffness of the construct. Locking a bone fastener into bone plate 100 can achieve angular and axial stability and eliminate the possibility for the bone fastener to toggle, slide, or be dislodged, reducing the risk of postoperative loss of reduction.

Slots 110 and/or 111 may include a plurality of variable angled slots formed therein for receiving a non-locking or variable angled (e.g., polyaxial) bone fastener. In use, the variable angled slots are arranged and configured to enable the bone fastener inserted therein to achieve a greater range of insertion angles as compared to, for example, a conventional locking screw that is threadably coupled to bone plate 100. For example, in some examples, the angular position of the bone fastener may be rotated through a range of approximately ±15 degrees, although the range of allowable polyaxial rotation can vary, including greater and less than the fifteen degrees. In use, the variable angled slots may be provided in any suitable manner, configuration, etc. now known or hereafter developed for enabling polyaxial positioning or angling of the bone fastener relative to bone plate 100.

In some examples, the variable angled slots may include fins or projections that extend radially inward from an inner surface of the slots and into an interior region of the slots, and which are configured to engage or cooperate with the head portion of the bone fastener. In use, the fins engage the head portion of the bone fastener in order to secure the bone fastener at a desired position and at a desired angular orientation within the variable angled slot. Non-limiting examples of variable angle slots and the operation and configuration of the fins can be found in U.S. Pat. No. 10,092,337, entitled "Systems and Methods for Using Polyaxial Plates;" U.S. patent application Ser. No. 13/524,506, entitled "Variable Angle Locking Implant;" and/or International PCT Patent Application No. WO20200247381, entitled "Orthopedic Implant with Improved Variable Angle Locking Mechanism."

Bone plate 100 may have a slot pattern of slots 110-112. In some examples, bone plate 100 may have a brim slot pattern of slots on brim segment 101 and a QLS slot pattern of slots on QLS segment 102. The slot pattern may include a number of slots 110-112, an orientation of slots 110-112, a placement of slots 110-112, a number of different types of slots 110-112, slot dimensions, distance between slots, and/or other features that contribute to the slot pattern.

As shown in FIGS. 1A and 1B, the slot pattern may include one elongated slot 112-1 on brim segment 101 and one elongated slot 112-2 on QLS segment 102. The QLS slot pattern may include all locking slots 111 except for elongated slot 112-2. The brim slot pattern may include a repeating pattern of non-locking slots 110-locking slots 111, with elongated slot 112-1 arranged between one non-locking slot 110 and one locking slot 111. Examples are not limited in this context.

Fasteners may be non-rigidly (or loosely) arranged through certain of slots 110-112, such that fasteners extend through slots 110-112 and into the pelvis 120, but are not tightened to fixedly clamp or hold bone plate 100 to pelvis 120. Accordingly, when fasteners are non-rigidly arranged in slots 110-112 (or a minimal number of slots 110-112), bone plate 100 may have a limited freedom of movement, for instance, rotation in a generally superior/inferior direction about line C as indicated by line D. A non-rigid fixation of bone plate 100 does not necessarily mean that bone plate 100 is "hanging" or moveable without force. In general, non-rigidly arranged fasteners allow for movement via manual (including via tools) force without overt effort or damaging the bone, tissue, or other structures.

In some examples, elongated slots 112 may be arranged to provide various types of movement, such as superior/inferior, medial/lateral, and/or the like. In some examples, an orientation of elongated slots 112 (for instance, the orientation of the longitudinal axis of elongated slots, which allow for movement about a fastener) may be configured to provide for one or more directions of movement. In some examples, various elongated slots 112 (or combinations thereof) may be used to provide one or more directions of movement. For example, elongated slots 112-1 and 112-2 may be used to facilitate superior/inferior movement. In another example, elongated slots 112-1 and 112-2 may not be used and another set of slots (not shown) may be arranged to provide for medial/lateral movement.

Fasteners non-rigidly arranged within slots 110 and/or 111 may allow only a very limited range of motion, for instance, less than 0.5 mm length of rotation. However, due to the elongated opening of elongated slots 112, bone plate 100 may have an increased range of motion with fasteners non-rigidly arranged therein. For example, bone plate 100 may have a range of motion of about 0.5 mm to about 2 mm when fasteners are non-rigidly arranged within elongated slots.

Accordingly, a bone plate according to some examples may be configured to allow a surgeon to shift or otherwise adjust the bone plate during an implantation procedure to provide final discrete movements of the bone plate to achieve an optimal fit on the patient pelvis structure. For example, it is challenging for surgeons to achieve an optimal fit on the pelvis during surgery using conventional plates because once fasteners become inserted, which also work to hold the plate in place for final implantation steps, fine, discrete movement of the plate is not possible. A surgeon may want to maintain the bone plate in place (without having to manually hold the bone plate), while allowing for small shifting adjustments (as opposed to the larger, typically erroneous movements with conventional devices that require correction). However, with the configurations of slot patterns, including through the use of elongated slots, inter-surgical shifting of a bone plate according to some examples is possible to achieve an optimal fit of the bone plate within the QLS and adjacent or on the pelvic brim.

Although bone plates are depicted in the present disclosure with various patterns of slots, not all slots require fastening during a medical procedure using a bone plate according to some examples. For example, fasteners may be used to affix a bone plate to a pelvis or other bone structure using less than all of the available slots.

Some examples may include a plate configuration process or method operative to determine a bone plate shape and/or slot pattern. In various examples, all or a portion of plate configuration process may be performed by a computer-implemented method via specifically programmed computer hardware and/or software. For example, all or a portion of plate configuration process may be performed by a computer-assisted surgery system (CASS) for performing computer- and/or robotic-assisted surgery on a patient.

In some examples, the plate configuration process may operate to determine the bone plate shape based on, inter alia, statistical mean pelvis models relating to the patient and/or associated patient population. In various examples, a slot pattern may be selected based on the type of implantation procedure, for example, to provide access to one or more elongated slots through an incision made during the implantation procedure. For instance, a first slot pattern may be selected for a middle window implantation procedure to allow for access to one or more particular slots via certain incisions and/or during certain steps of the specific procedure, a second slot pattern may be selected for a Stoppa procedure, and so on. In some examples, the slot pattern of the elongated slots may allow for movement of the bone plate about fasteners arranged therein in a superior-inferior or substantially superior-inferior direction.

In some examples, a bone plate may be configured with plate contour to provide extra coverage on the pelvic brim (e.g., from pubic tubercle to close to the sacroiliac (SI) joint). A bone plate may be formed of malleable material such that the bone plate may be manually or semi-manually contoured for a final fit as necessary.

In some examples, non-locking and variable-angle locking holes may be used on the brim segment, which may address various bone issues, including, without limitation, to address geriatric population needs. For instance, variable-angle locking slots in the QLS segment may operate to allow screw angulation and fracture fixation in the presence of poor-quality bone. In some examples, elements, such as bars (for instance, segment 133) and/or holes on quadrilateral portion may be used by clamps or other devices for compressing the bone plate to the bone and for lateralization.

FIGS. 2A-2F depict multiple views of a suprapectineal bone plate in accordance with the present disclosure. As shown in FIGS. 2A-2F, bone plate 100 may include a suprapectineal bone plate having a brim segment 101 coupled to a QLS segment 102 via bridges 103. Bone plate 100 includes a slot pattern of slots 110-212. Bone plate 100 includes two elongated slots 112 arranged on brim segment 101 and one elongated slot 112 arranged on QLS segment 102. The QLS slot pattern includes a plurality of slots 110-212 having a majority of locking slots 111 (for instance, 8 out of 11 slots are locking slots). The brim slot pattern includes an alternating pattern of non-locking slots 110-locking slots 111, with elongated slots 112 arranged between certain other slots.

Figure 3:
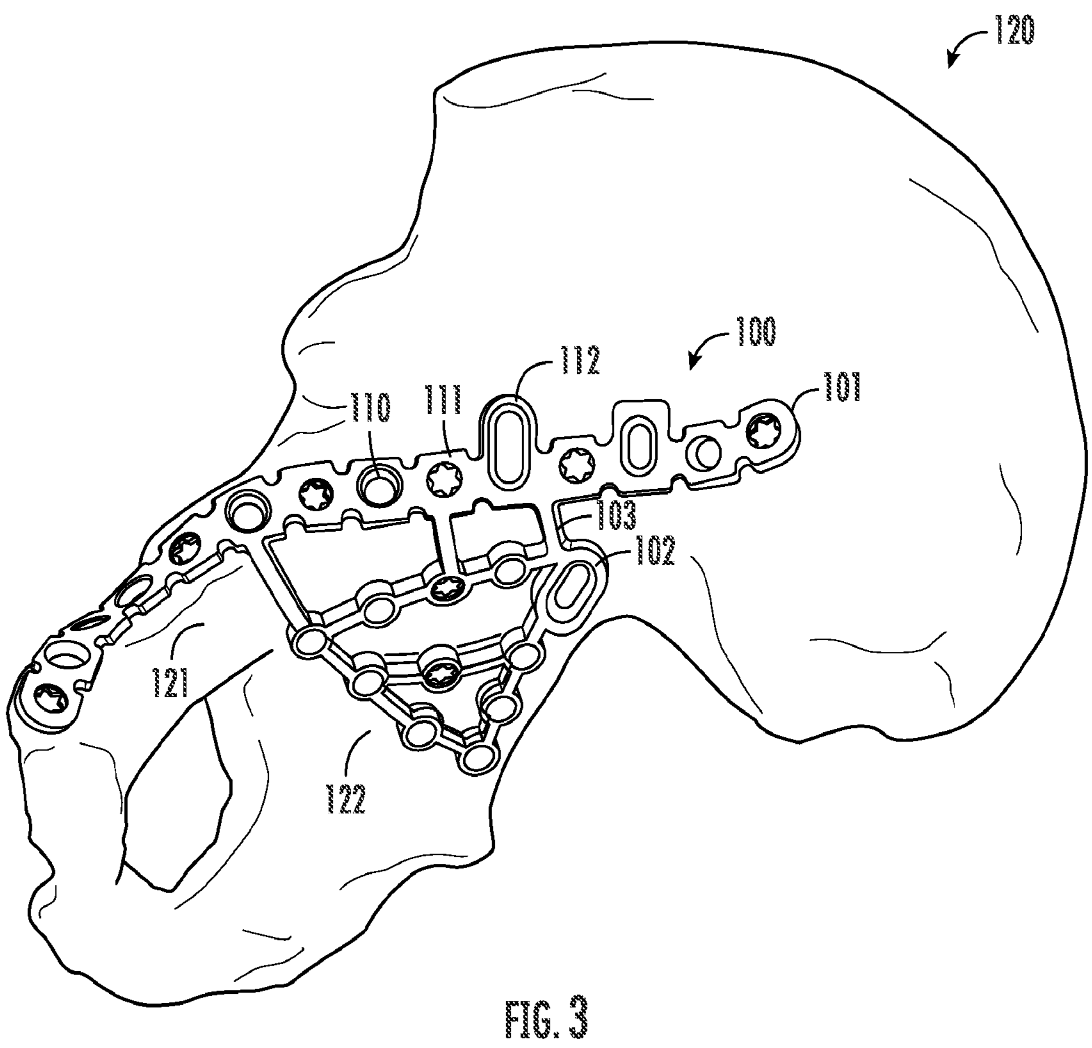
FIG. 3 depicts a suprapectineal bone plate implanted on a pelvis in accordance with the present disclosure.
Figure 4A:
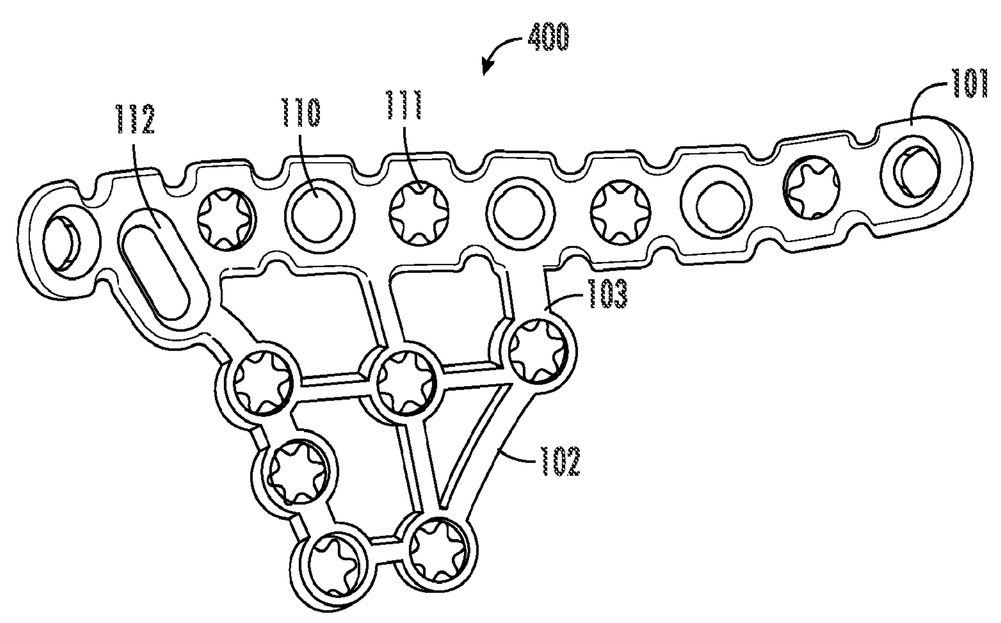
FIGS. 4A-4F depict multiple views of an infrapectineal bone plate in accordance with the present disclosure.
Figure 4B:
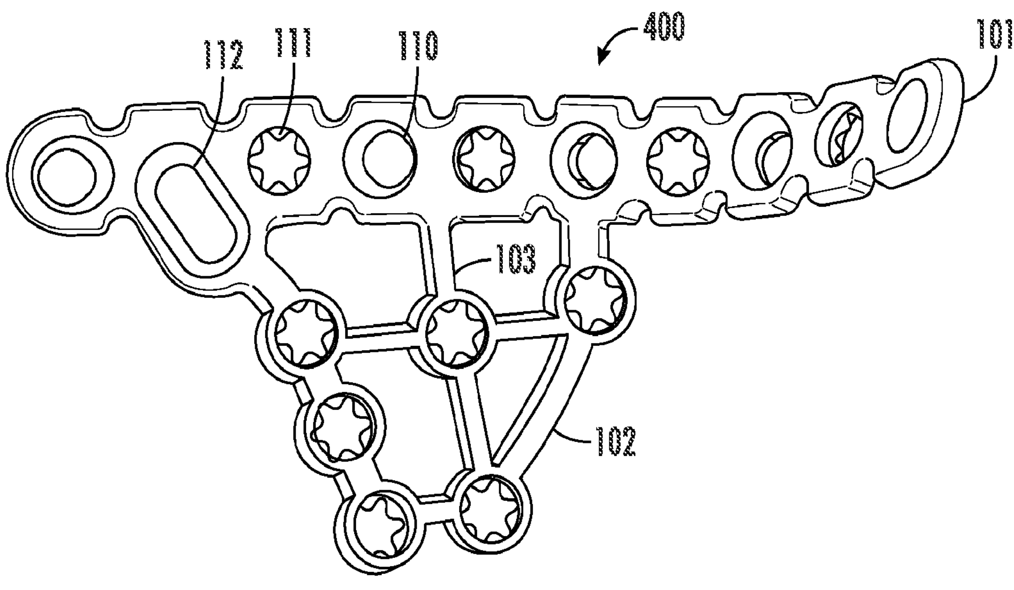
Figure 4C:
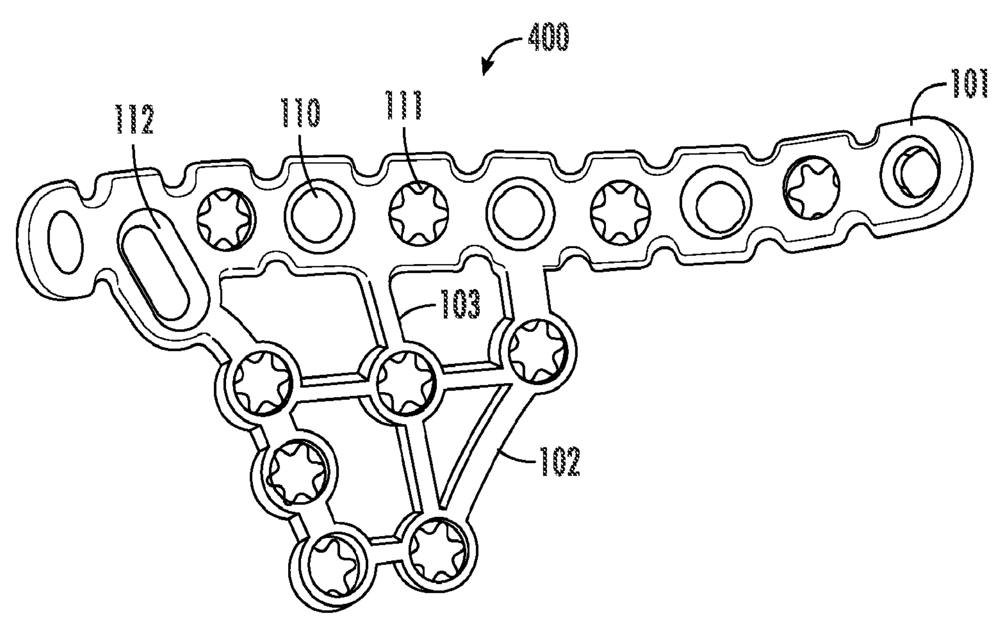
Figure 4D:
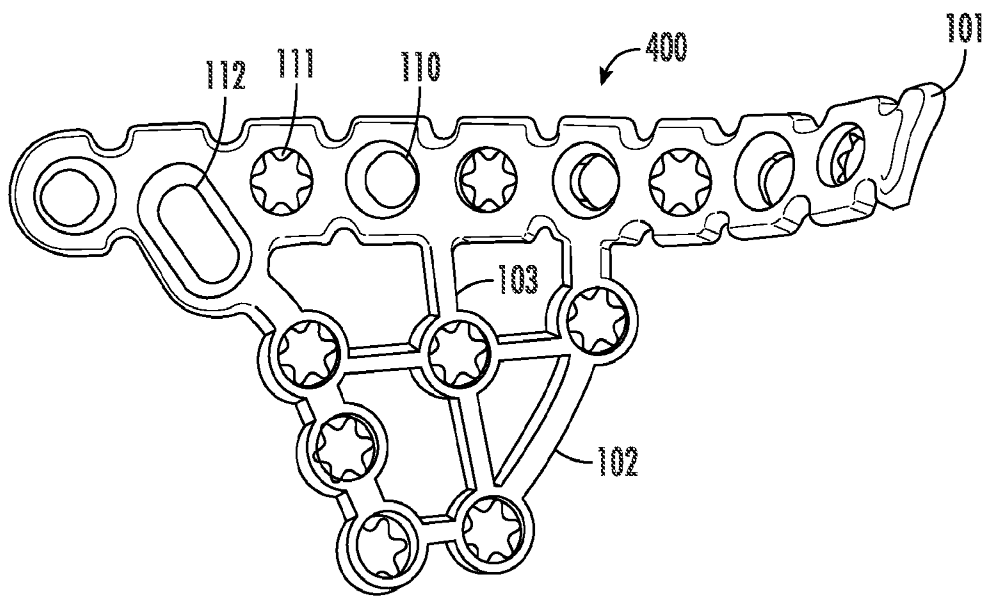
Figures 4E, 4F:
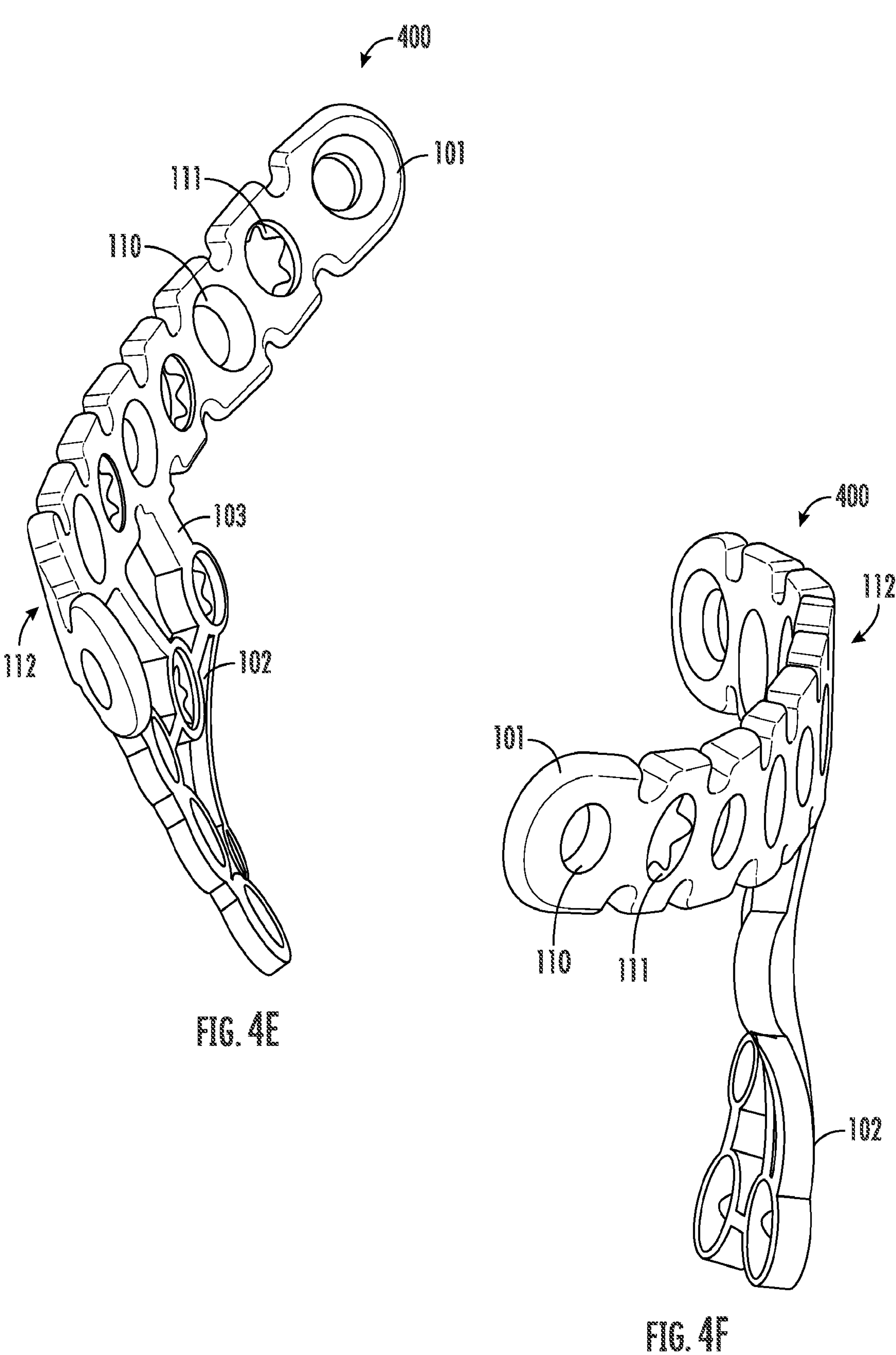

FIG. 3 depicts a suprapectineal bone plate implanted on a pelvis in accordance with the present disclosure. As shown in FIG. 3, a bone plate 100 may include a suprapectineal bone plate having a brim segment 101 coupled to a QLS segment 102 via bridges 103. Bone plate 100 may be configured to have brim segment 101 affixed on or over a pelvic brim 321 of pelvis 320, and QLS segment 102 affixed to QLS 322 of pelvis 320.

FIGS. 4A-4F depict multiple views of an infrapectineal bone plate in accordance with the present disclosure. As shown in FIGS. 4A-4F, bone plate 400 may include an infrapectineal bone plate having a brim segment 101 coupled to a QLS segment 102 via bridges 103. Bone plate 400 includes a slot pattern of slots 110-112. Bone plate 400 includes one elongated slot 112 arranged on brim segment 101 and no elongated slots 112 arranged on QLS segment 102. The QLS slot pattern includes a plurality of slots 110-112 all configured as locking slots 111. The brim slot pattern includes an alternating pattern of non-locking slots 110-locking slots 111, with elongated slot 112 arranged between a non-locking slot 110 and a locking slot 111 and coupled directly to a bridge 103.

Figure 5:
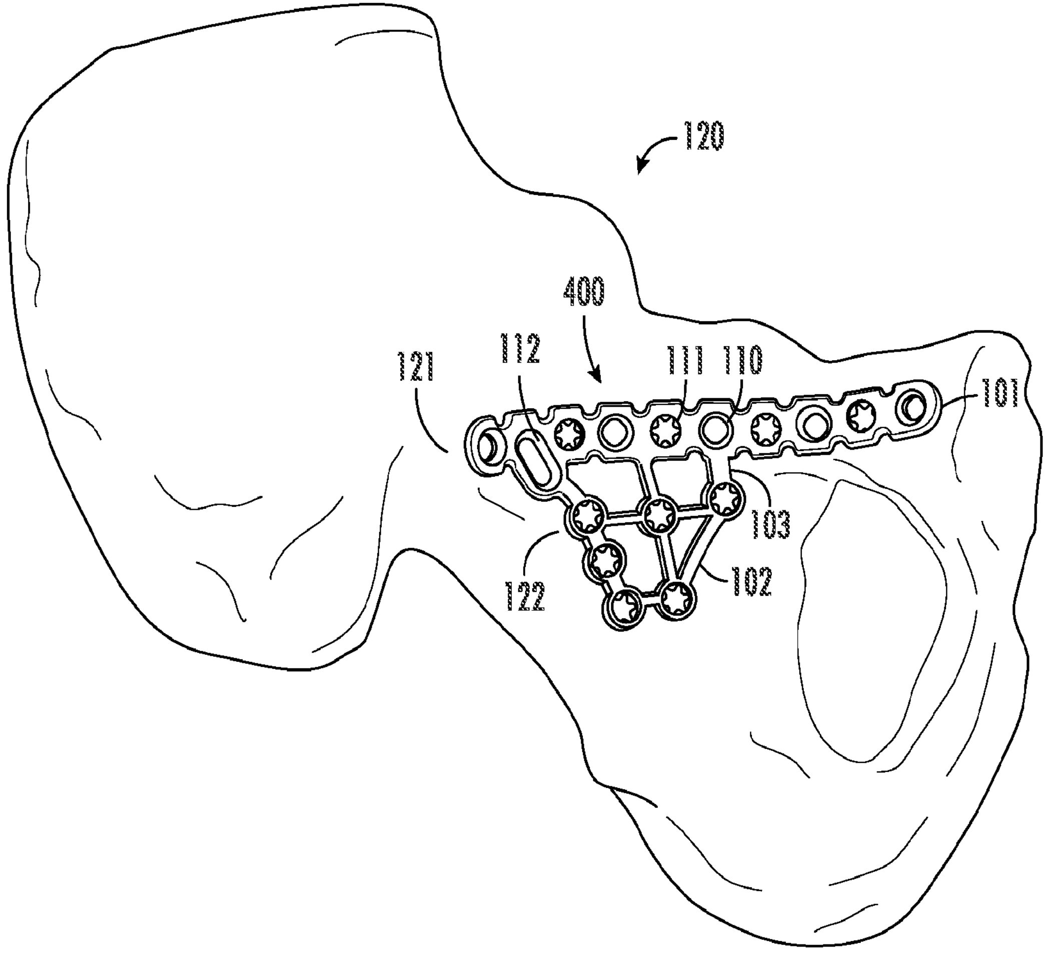
FIG. 5 depicts an infrapectineal bone plate implanted on a pelvis in accordance with the present disclosure.
Figure 6A:
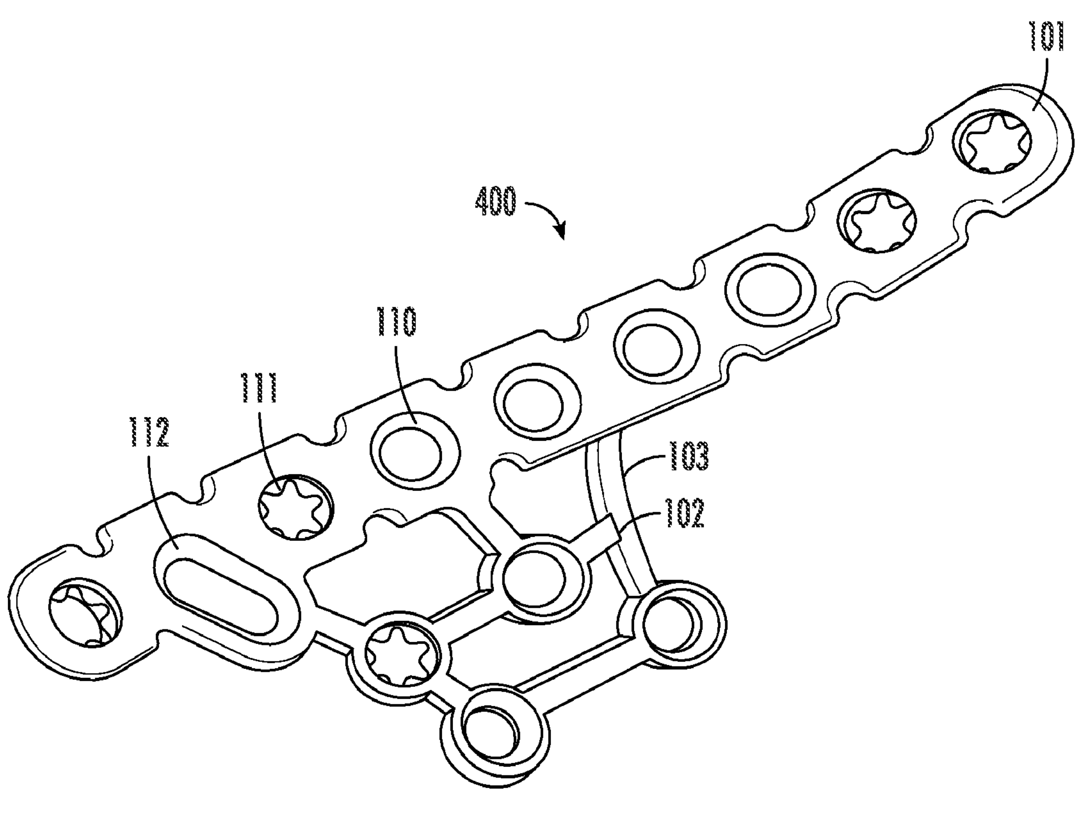
FIGS. 6A-6H depict multiple views of an infrapectineal bone plate in accordance with the present disclosure.
Figure 6B:
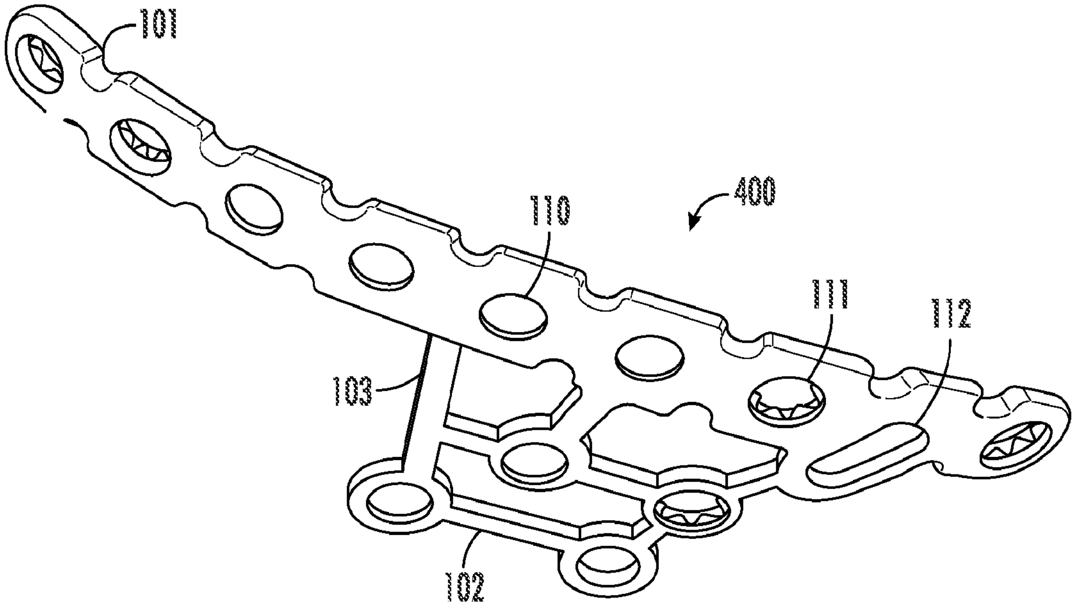
Figure 6C:
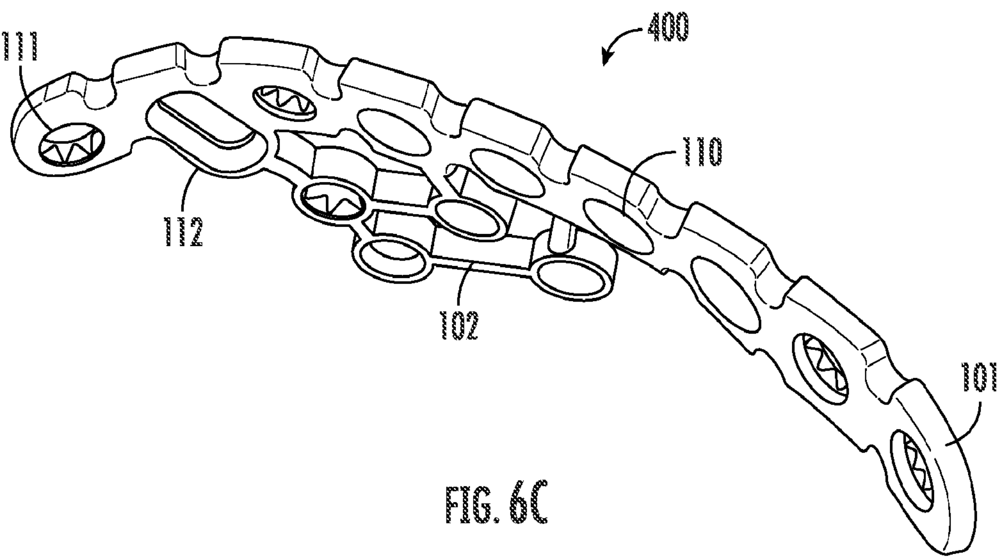
Figure 6D:
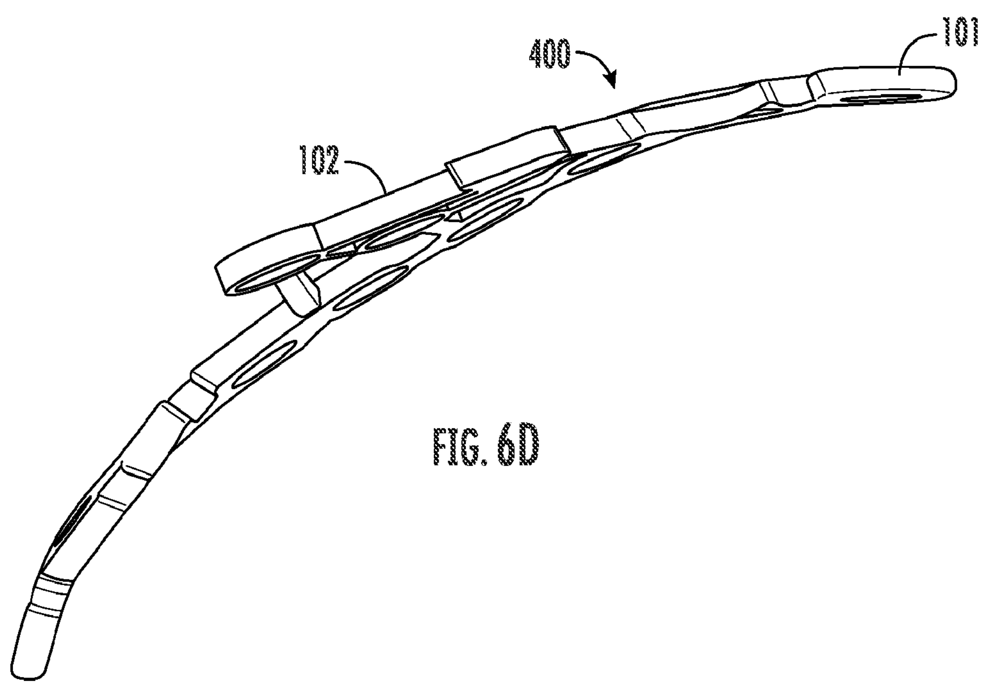
Figure 6E:
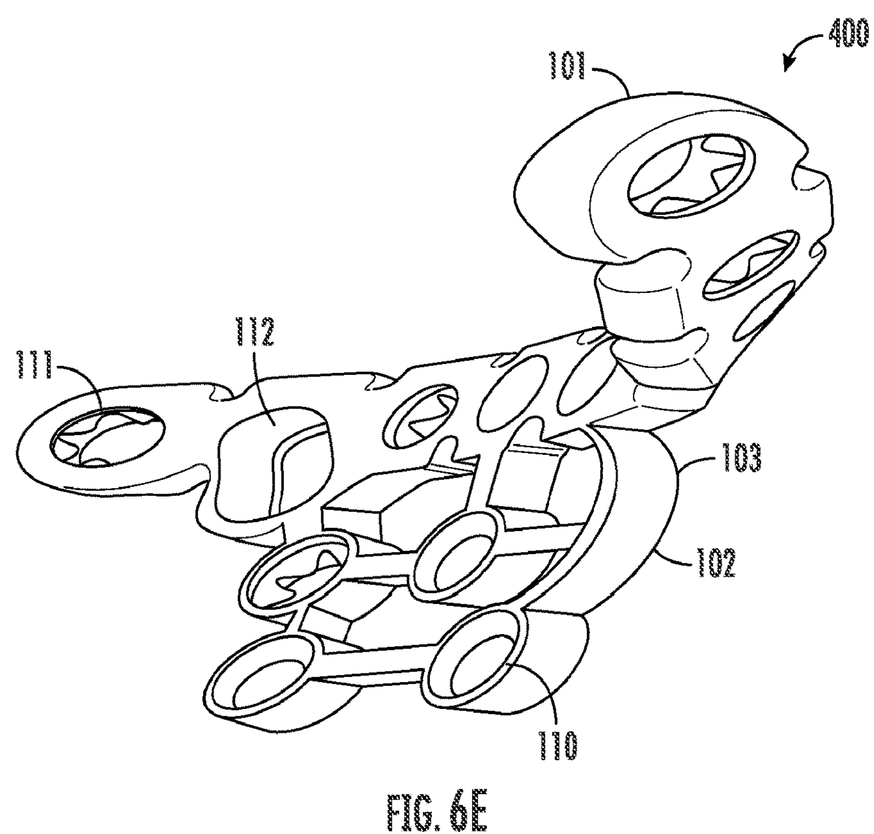
Figure 6F:
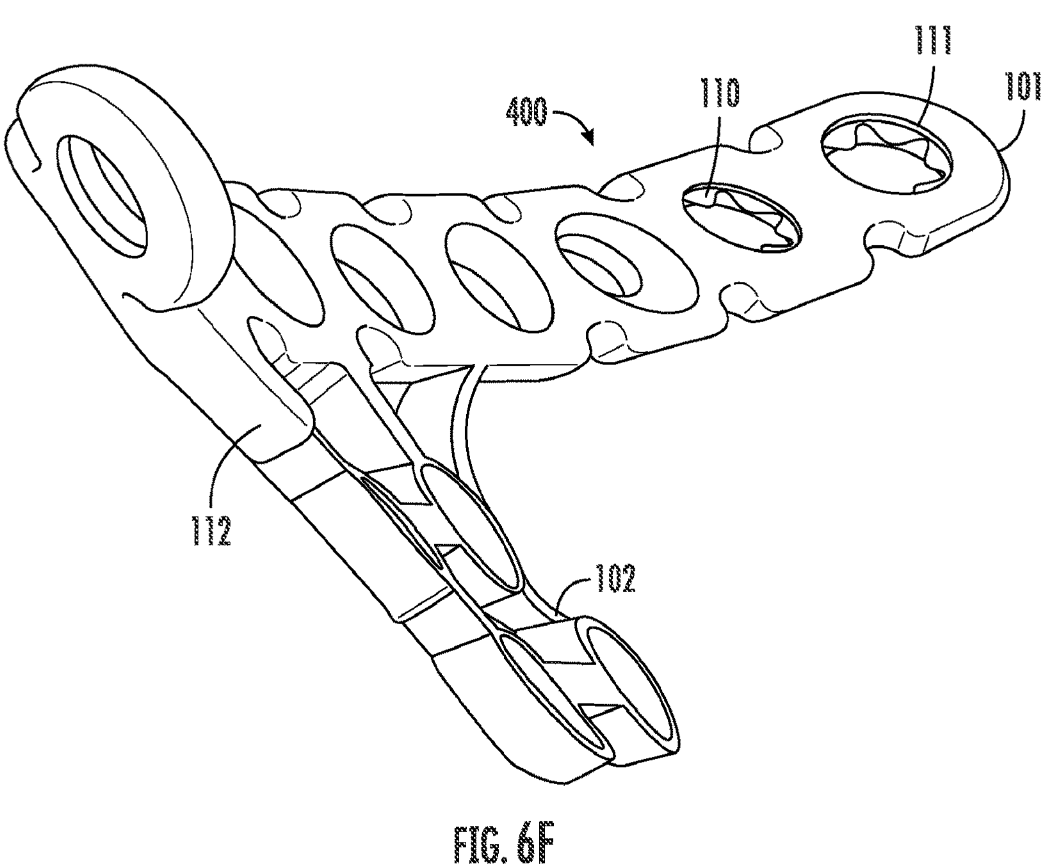
Figure 6G:
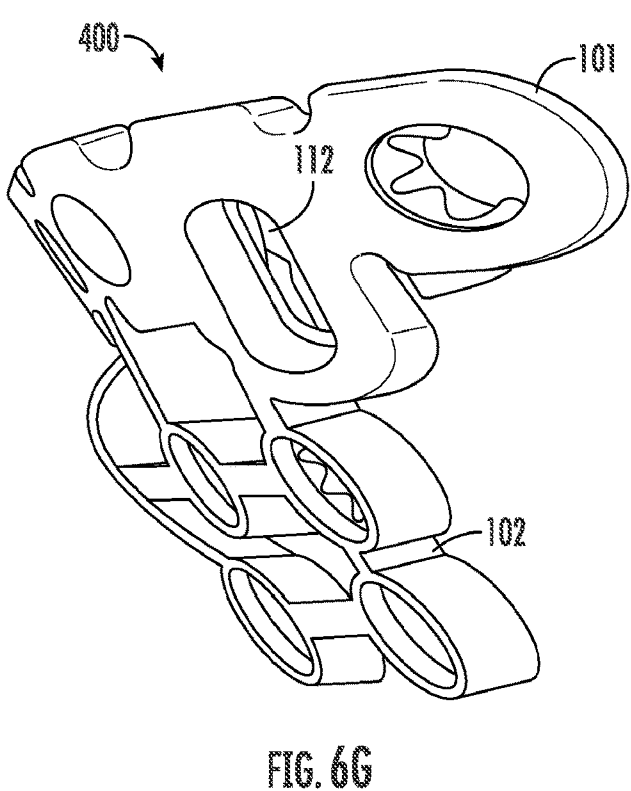
Figure 6H:
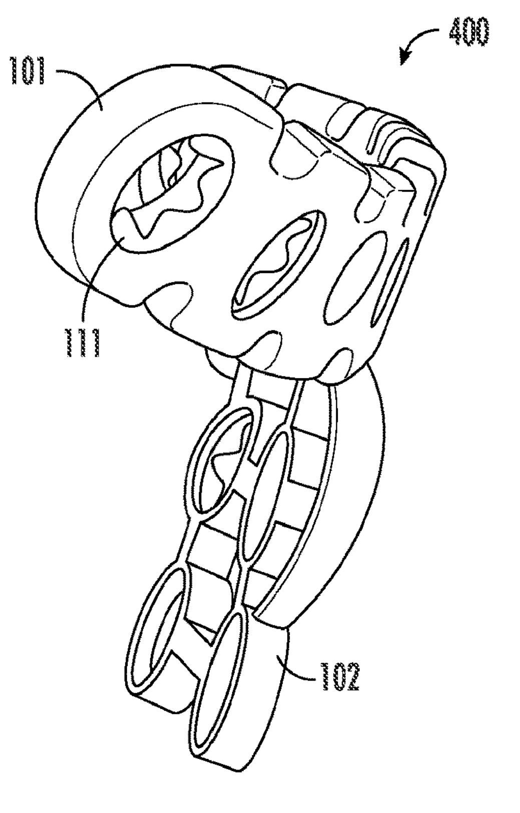
Figure 7A:
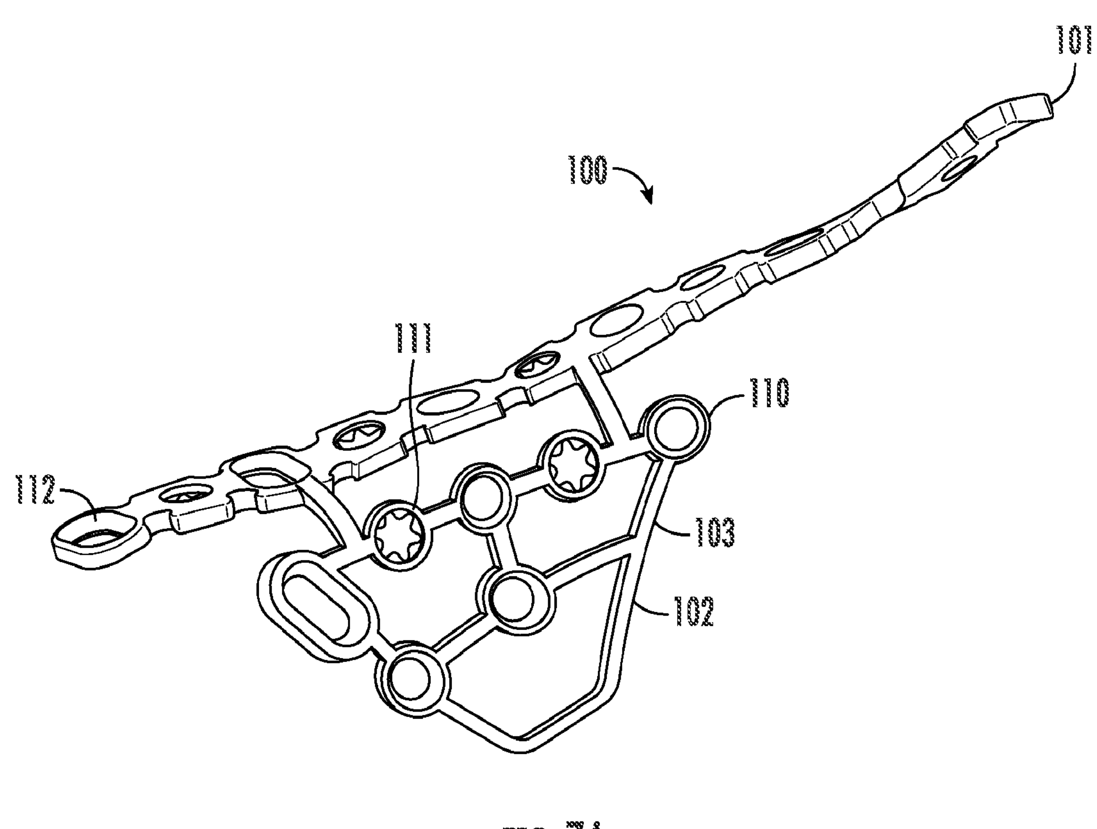
FIGS. 7A-7H depict multiple views of a suprapectineal bone plate in accordance with the present disclosure.
Figure 7B:
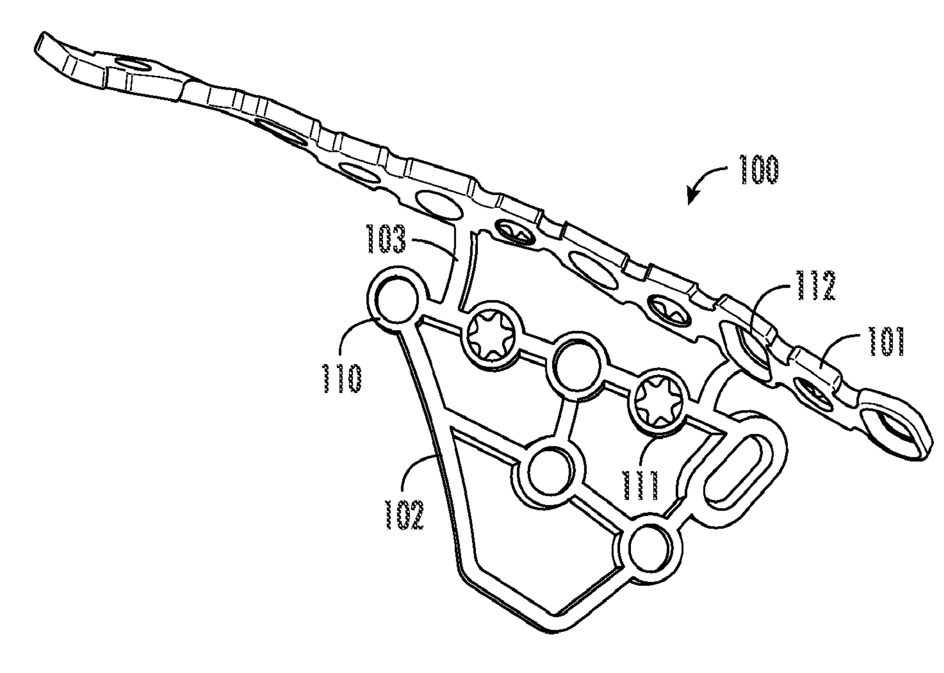
Figure 7C:
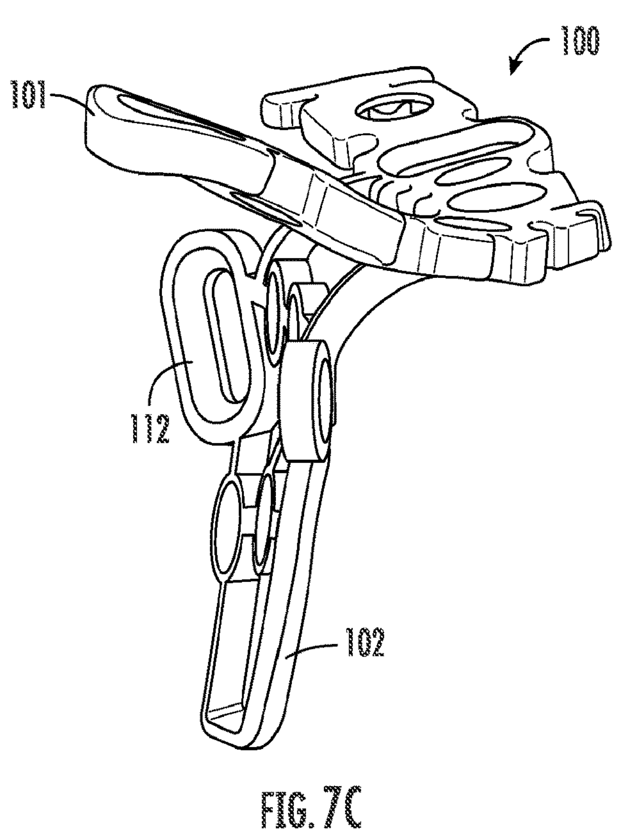
Figure 7D:
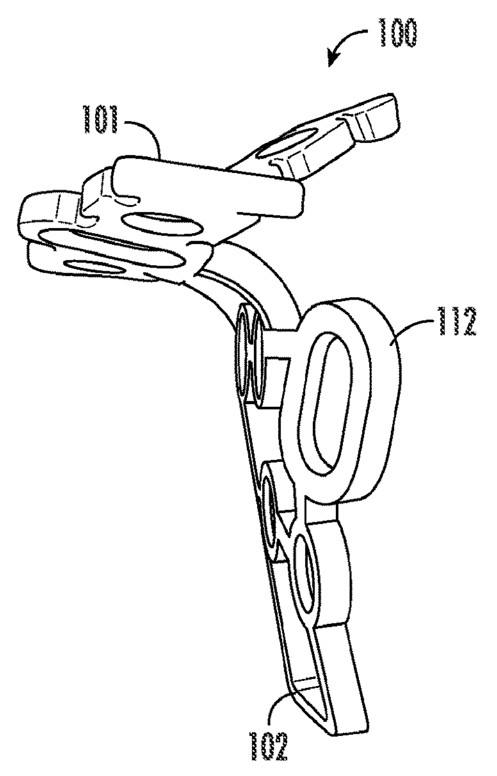
Figure 7E:
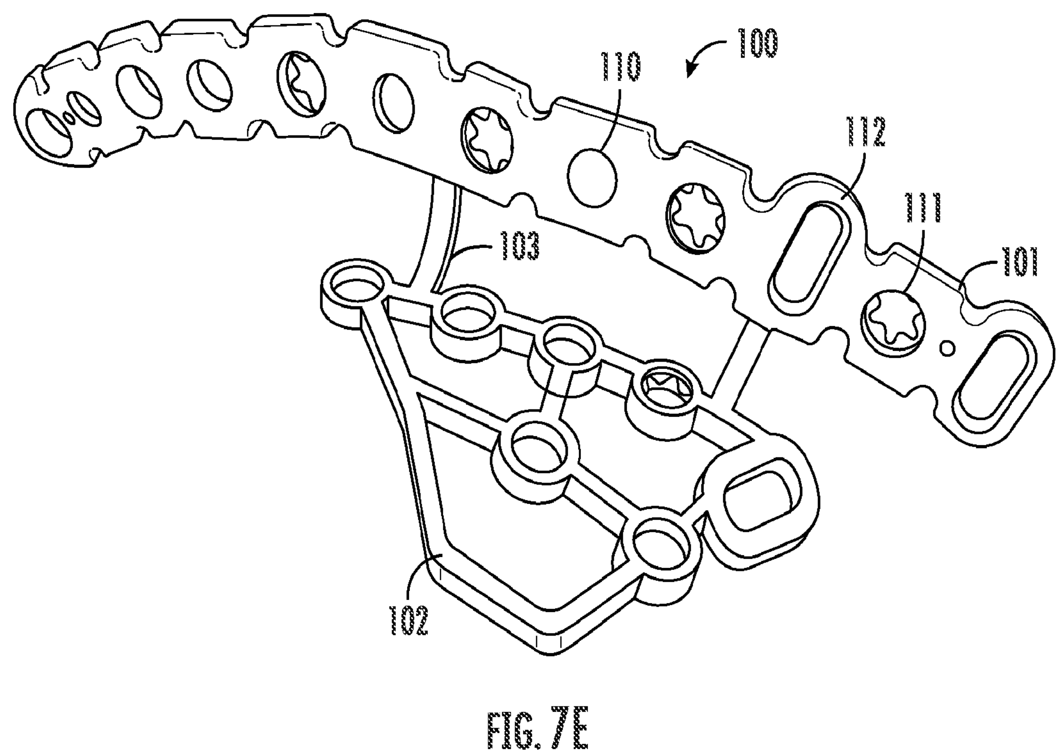
Figure 7F:
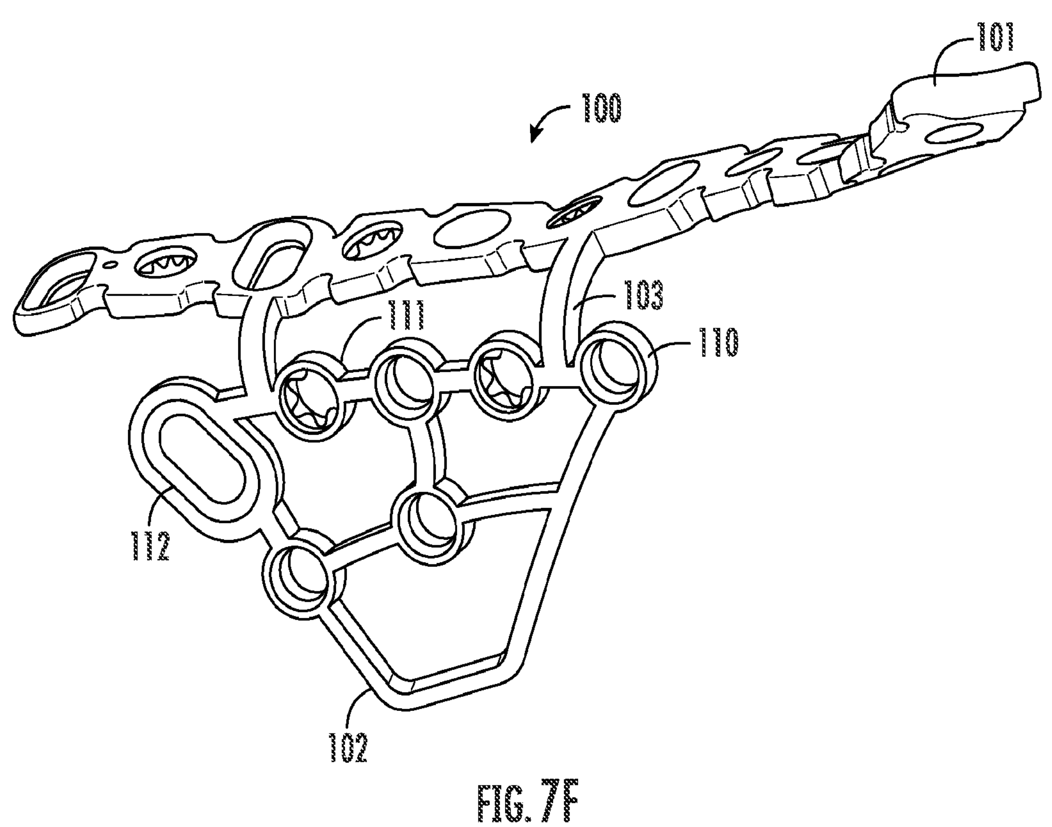
Figure 7G:
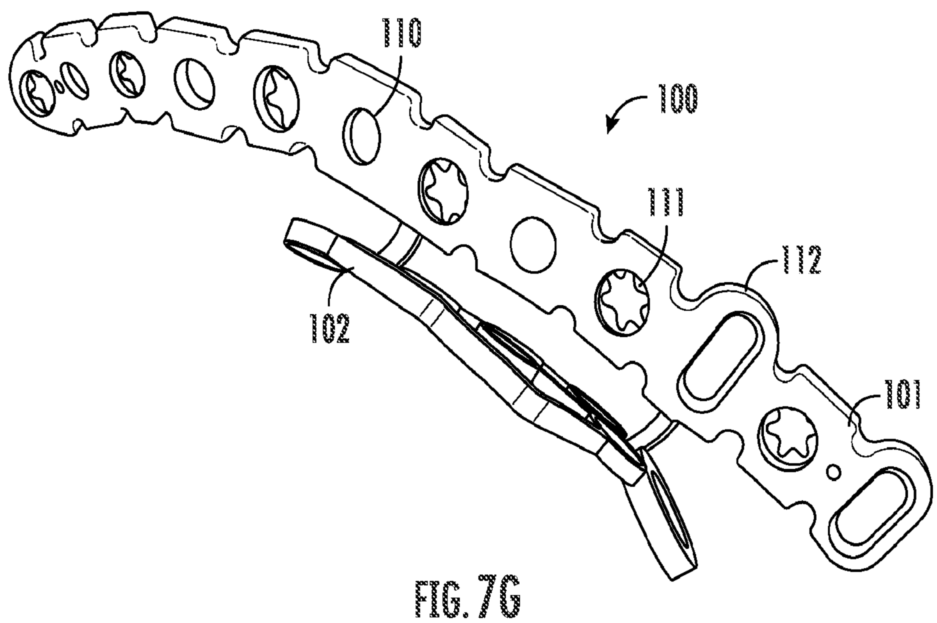
Figure 7H:
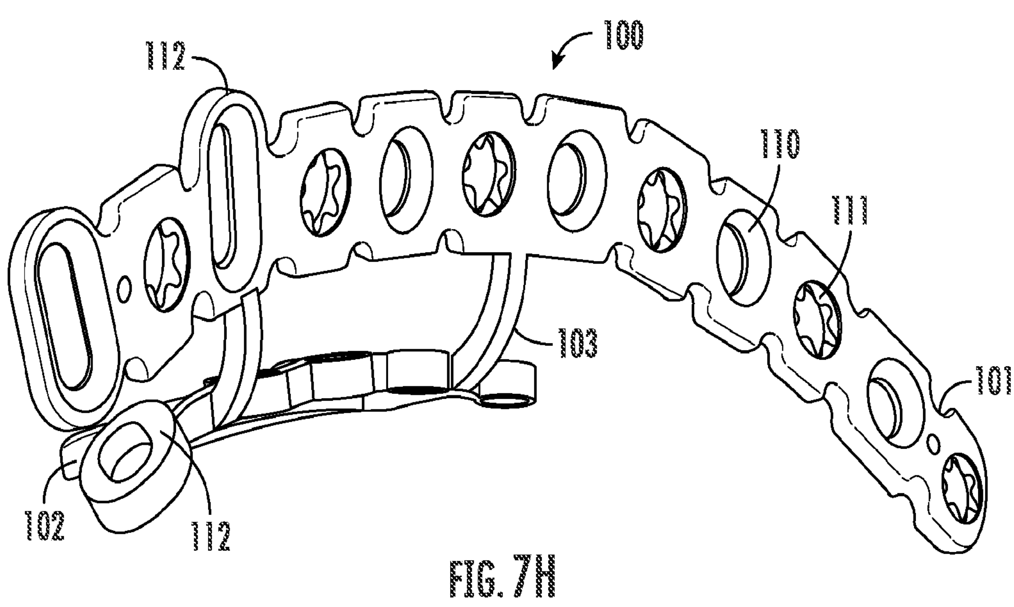

FIG. 5 depicts an infrapectineal bone plate implanted on a pelvis in accordance with the present disclosure. As shown in FIG. 5, a bone plate 400 may include an infrapectineal bone plate having a brim segment 101 coupled to a QLS segment 102 via bridges 103. Bone plate 400 may be configured to have brim segment 101 affixed directly adjacent, but below or substantially below, pelvic brim 521 of pelvis 520, and QLS segment 102 affixed to QLS 522 of pelvis 520.

FIGS. 6A-6H depict multiple views of an infrapectineal bone plate in accordance with the present disclosure. As shown in FIGS. 6A-6H, bone plate 400 may include an infrapectineal bone plate having a brim segment 101 coupled to a QLS segment 102 via bridges 103. Bone plate 400 includes a slot pattern of slots 110-112.

FIGS. 7A-7H depict multiple views of a suprapectineal bone plate in accordance with the present disclosure. As shown in FIGS. 7A-7H, bone plate 400 may include a suprapectineal bone plate having a brim segment 101 coupled to a QLS segment 102 via bridges 103. Bone plate 100 includes a slot pattern of slots 110-112.

Figure 8:
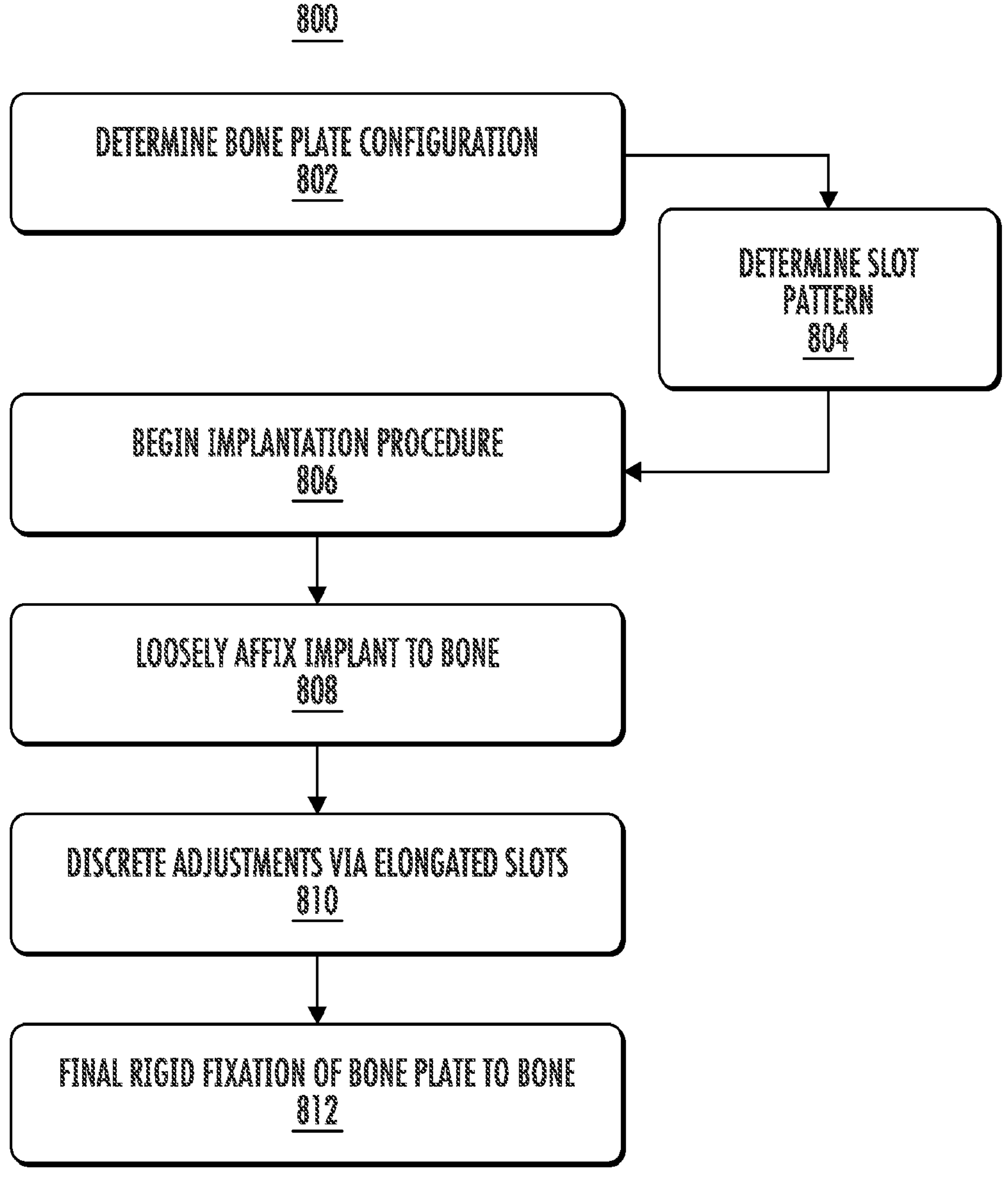
FIG. 8 illustrates an example of a method flow in accordance with the present disclosure.

FIG. 8 illustrates an example of a method flow 800. Method flow 800 may be representative of some or all of the operations of a bone plate implantation process for implanting a bone plate configured according to some examples herein, for example, by an operator (for example, a surgeon), a logic device (for example, a CAS system), or a combination thereof.

Method flow 800 may include determining a bone plate configuration at block 802. For example, a surgeon or other healthcare professional may determine properties of a bone plate based on certain patient characteristics, preferences, and/or the like. Non-limiting properties may include materials, size, pre-formed contours of brim segments, QLS segments, and/or the like. In some examples, determining the bone plate configuration may include determining a slot pattern at block 804. In some examples, a slot pattern may be determined based on patient characteristics, such as bone strength and quality, area of target surfaces (for instance, QLS, pelvic brim), and/or the like. In various examples, at least a portion of slot pattern may be determined based on the implantation procedure, such as the selection of elongated slots based on access incisions during a particular implantation procedure.

At block 806, method flow 800 may include beginning the implantation procedure. Block 806 is an interoperable stage including performance of particular implantation procedure (for instance, a middle window procedure) on a patient based on a surgical plan. During the implantation procedure, the bone plate is implanted in the patient through one or more incisions.

Method flow 800 may include loosely affixing the implant to the bone at step 808. For example, one or more fasteners may be inserted into the bone via slots in the bone plate, including one or more elongated slots. The bone plate may be held in place during non-rigid or loose affixation, but may be moved about elongated slots according to some examples via manual force.

At block 810, the method flow 800 may include making discrete adjustments to the position of the bone plate via the movement allowed through the elongated slots. For instance, with reference to FIG. 1A, a surgeon may move bone plate 100 about line A (e.g., superior-inferior movement) about line C. In this manner, a surgeon may arrange the bone plate at an optimal location via movement of the bone plate about the pelvis allowed through the elongated slots.

Method flow 800 may include a final rigid fixation of the bone plate to the bone at step 812. Once the optimal fit has been achieved, the surgeon may rigidly insert the fasteners through the slots to affix the bone plate to the bone. Once the bone plate is rigidly affixed, manual force does not allow for movement of the bone plate about the pelvis.

In accordance with the various features described herein, in use, a set or kit of bone plates containing a relatively reduced number of bone plates, including, for example, one bone plate, that may be implanted adjacent to a bone, such as a pelvis. In accordance with the features described herein, bone plates providing adequately rigidity or strength are disclosed while still providing sufficient flexibility to fit a patient's pelvis and to facilitate the effective and efficient installation of the bone plates at an optimal location on the pelvis are disclosed. In addition, the bone plate may include a hole pattern inclusive of locking slots, non-locking slots, variable angled slots, and/or elongated slots providing for a reduction in the number of different plate lengths needed in a functional set.

The foregoing description has broad application. Accordingly, the discussion of any example or embodiment is meant only to be explanatory and is not intended to suggest that the scope of the disclosure, including the claims, is limited to these examples or embodiments. In other words, while illustrative examples of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one," "one or more," and "and/or," as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order, and relative sizes reflected in the drawings attached hereto may vary.

What is claimed is:

1. A suprapectineal or infrapectineal bone plate system, comprising:

bone fasteners including a first fastener and a second fastener; and a suprapectineal or infrapectineal bone plate comprising:

a brim segment coupled to a quadrilateral surface (QLS) segment via at least one bridge, wherein the brim segment is configured to be affixed to one of a portion of a pelvic brim or the quadrilateral surface (QLS) below the pelvic brim of a patient, the QLS segment is configured to be arranged directly adjacent to the QLS of the pelvis;

a plurality of slots arranged on the brim segment, at least a portion of the plurality of slots configured to receive the first fastener to affix the bone plate to the pelvic brim or the quadrilateral surface (QLS) below the pelvic brim, the plurality of slots comprising at least one elongated slot configured to receive the second fastener to non-rigidly affix the bone plate to the pelvic brim or the quadrilateral surface (QLS) below the pelvic brim to facilitate adjustment of the bone plate in a first adjustment direction during an implantation procedure; and a plurality of slots arranged on the QLS segment including at least one elongated slot arranged on the QLS segment, wherein each elongated slot comprises a short dimension with opposing sides that are in contact with the second fastener when the second fastener is arranged within the elongated slot to prevent movement of the bone plate in a short direction, and a long dimension configured to allow linear movement of the bone plate in a second adjustment direction when the bone plate is non-rigidly affixed to the pelvic brim or the quadrilateral surface (QLS) below the pelvic brim, and wherein the at least one bridge is malleable and configured to allow pre-operative and/or inter-operative changing of a position of the brim segment relative to the QLS segment.

2. The bone plate system of claim 1, wherein the first adjustment direction is one of a medial/lateral direction or a superior/inferior direction and the second adjustment direction is one of a medial/lateral direction or a superior/inferior direction.

3. The bone plate system of claim 1, wherein the at least one elongated slot on the brim segment has the first adjustment direction of medial/lateral and the at least one elongated slot on the QLS segment has the second adjustment direction of superior/inferior.

4. The bone plate system of claim 1, wherein the bone plate is a suprapectineal bone plate wherein the brim segment is configured to be affixed on the pelvic brim.

5. The bone plate system of claim 1, wherein the bone plate is an infrapectineal bone plate wherein the brim segment is configured to be affixed to the QLS below the pelvic brim.

6. The bone plate system of claim 1, wherein the plurality of slots arranged on the brim segment comprises at least one non-locking slot and at least one locking slot.

7. The bone plate system of claim 1, the plurality of slots arranged on the brim segment in a brim slot pattern comprising alternating locking slots and non-locking slots arranged along a longitudinal length of the brim segment.

8. The bone plate system of claim 7, the brim slot pattern comprising the at least one elongated slot arranged between a locking slot and a non-locking slot of the brim slot pattern.

9. The bone plate system of claim 1, the plurality of slots arranged on the brim segment comprising at least one set of elongated slots configured to facilitate movement in one set adjustment direction.

10. The bone plate system of claim 9, the at least one set comprising one of a medial/lateral adjustment set or a superior/inferior adjustment set.

11. The bone plate system of claim 1, the at least one elongated slot arranged on the brim segment comprising a plurality of slots arranged at a slot orientation angle with respect to the at least one elongated slot arranged on the QLS segment.

12. The bone plate system of claim 1, the at least one elongated slot arranged on the brim segment is configured to facilitate movement of about 1 mm to about 10 mm and/or the at least one elongated slot arranged on the QLS segment is configured to facilitate movement of about 1 mm to about 10 mm.

13. The bone plate system of claim 1, wherein the at least one elongated slot on the brim segment is angled with an inter-slot orientation angle with respect to the at least one elongated slot on the QLS segment.

* * * * *